(12) United States Patent
Gengrinovitch et al.

(10) Patent No.: US 7,989,188 B2
(45) Date of Patent: Aug. 2, 2011

(54) CONJUGATES FOR CANCER THERAPY AND DIAGNOSIS

(75) Inventors: Stela Gengrinovitch, Doar Na Merom Galil (IL); Esther Izakovich, Kiryat Bialik (IL)

(73) Assignee: BioSight Ltd., Karmiel (IL)

(*) Notice: Subject to any disclaimer, the term of this patent is extended or adjusted under 35 U.S.C. 154(b) by 348 days.

(21) Appl. No.: 11/497,511

(22) Filed: Aug. 2, 2006

(65) Prior Publication Data

US 2007/0072800 A1    Mar. 29, 2007

Related U.S. Application Data

(63) Continuation of application No. PCT/IL2005/000117, filed on Feb. 2, 2005.

(60) Provisional application No. 60/540,334, filed on Feb. 2, 2004.

(51) Int. Cl.
*C12P 13/04* (2006.01)
*A01N 43/48* (2006.01)
*G01N 33/574* (2006.01)

(52) U.S. Cl. ............ 435/106; 514/45; 514/49; 435/7.23

(58) Field of Classification Search .................... None
See application file for complete search history.

(56) References Cited

U.S. PATENT DOCUMENTS

| | | | | |
|---|---|---|---|---|
| 2,949,451 A | 8/1960 | Hoffer | | 260/211.5 |
| 3,041,335 A | 6/1962 | Hoffer | | 260/242 |
| 4,179,337 A | 12/1979 | Davis et al. | | 435/181 |
| 4,296,105 A | 10/1981 | Baurain et al. | | 424/180 |
| 4,348,522 A | 9/1982 | Schultz et al. | | 544/358 |
| 4,401,592 A | 8/1983 | Yoshikumi et al. | | 260/112 B |
| 4,587,046 A * | 5/1986 | Goodman et al. | | 530/330 |
| 4,859,764 A | 8/1989 | Drent et al. | | 528/392 |
| 5,106,951 A | 4/1992 | Morgan, Jr. et al. | | 530/391 |
| 5,643,957 A | 7/1997 | Leone-Bay et al. | | 514/563 |
| 5,650,386 A | 7/1997 | Leone-Bay et al. | | 514/2 |
| 5,962,216 A | 10/1999 | Trouet et al. | | 435/4 |
| 6,344,213 B1 | 2/2002 | Leone-Bay et al. | | 424/451 |
| 6,428,780 B2 | 8/2002 | Leone-Bay et al. | | 424/85.1 |
| 6,605,638 B1 | 8/2003 | Kozak et al. | | 514/506 |
| 6,617,306 B2 | 9/2003 | Stein et al. | | 514/2 |
| 6,623,731 B2 | 9/2003 | Leone-Bay et al. | | 424/85.2 |

FOREIGN PATENT DOCUMENTS

| | | |
|---|---|---|
| WO | WO 96/30036 | 10/1996 |
| WO | WO 97/36480 | 10/1997 |
| WO | WO 03/006491 A2 | 1/2003 |

OTHER PUBLICATIONS

Giammona, 1992, Eur. J. Pharm. Biopharm., (EJPB) 38, 159-162.*
Yan, 2001, Journal of Bioactive and compatible Polymers, 16, 277-293.*
Giammona, 1992, Eur. J. Pharm. Biopharm., 38, 159-162.*
Matsumoto, 1975, Chemical & pharmaceutical bulletin vol. 23, pp. 106-113.*
Driscoll, 1979, Journal of Pharmaceutical Sciences, vol. 68 Issue 12, pp. 1519-1521.*
Hatzidakis, 2002, Anal. Chem., 74, 2513-2521.*
Hofman, 1985, Clin. Chem., 31, 1478-1480.*
Maruo, 1999, Chem. Coomun., 74, 2057-2058.*
Grant, 1992, Synthetic Peptides, A User's Guide, pp. 11-24.*
Wehland, 1977, PNAS, 74, 5613-5617.*

* cited by examiner

*Primary Examiner* — Andrew D Kosar
*Assistant Examiner* — Satyanarayana R Gudibande
(74) *Attorney, Agent, or Firm* — Winston & Strawn LLP

(57) ABSTRACT

The present invention relates to conjugates of a drug and an amino acid or an amino acid derivative or analog, pharmaceutical compositions that include the conjugates and methods of use thereof. In particular, the present invention relates to conjugates of anti-proliferative drugs and asparagine and glutamine and analogs thereof as compositions for treatment of cancer, and conjugates of imaging agent carriers and amino acids for the diagnosis of tumors and metastases.

12 Claims, 6 Drawing Sheets

CONJUGATES FOR CANCER THERAPY AND DIAGNOSIS

CROSS-REFERENCE TO RELATED APPLICATIONS

This application is a continuation of International application PCT/IL2005/000117 filed Feb. 2, 2005, which application claims the benefit of U.S. provisional application No. 60/540,334 filed Feb. 2, 2004, the entire content of each of which is expressly incorporated herein by reference thereto.

FIELD OF THE INVENTION

The present invention relates to conjugates comprising a chemotherapeutic agent and an amino acid or a derivative thereof, which are readily taken up by a target cell. In particular, the present invention relates to conjugates comprising anti-proliferative drugs and asparagine or glutamine and analogs thereof, pharmaceutical compositions comprising the conjugates and methods for the treatment of cancer using the compositions.

BACKGROUND OF THE INVENTION

Anti-Proliferative Drugs

Anti-proliferative drugs, also known as anti-metabolites, anti-neoplastic agents and covalent DNA binding drugs, act by inhibiting essential metabolic pathways and are commonly used in the treatment of malignant diseases. However, their high toxicity to normal cells and severe side effects limit their use as therapeutic agents. Undesirable side effects include inter alia anemia, emesis and balding due to cytotoxic effects on rapidly dividing normal cells, such as stem cells in the bone marrow, epithelial cells of the intestinal tract, hair follicle cells, etc.

Another major problem associated with anti-proliferative drugs is inherent or acquired resistance of tumors to the drugs. For example, although the initial remission rate following treatment with L-asparaginase is quite high in acute lymphoblastic leukemia (ALL) patients, relapse and associated drug resistance pose a significant clinical problem.

Studies have demonstrated increased asparagine synthetase (AS) expression in asparaginase-resistant cells, which has led to the hypothesis that elevated AS activity permits drug-resistant survival of malignant cells (Aslanian, et al, 2001).

Drug Resistance

Multi-drug resistance (MDR), the resistance of cells to a broad spectrum of structurally unrelated cytotoxic drugs, is a severe problem in the clinic.

Many of the prevalent forms of human cancer resist effective chemotherapeutic intervention. Some tumor populations, especially adrenal, colon, jejunal, kidney and liver carcinomas, appear to have drug-resistant cells at the outset of treatment (Barrows, 1995). In other cases, a resistance-conferring genetic change occurs during treatment; the resistant daughter cells are able to proliferate in the environment of the drug. Whatever the cause, resistance often terminates the value of an anti-proliferative drug.

Clinical studies suggest that a common form of multidrug resistance in human cancers results from expression of the mdr1 gene that encodes P-glycoprotein, a plasma membrane, energy-dependent, multidrug efflux pump. The influx of chemotherapeutic agents into cells occurs mainly by passive diffusion across the cell membrane, driven by the drug's electrochemical-potential gradient. In MDR cells, P-glycoprotein actively pumps the drug out of the cells, reducing its intracellular concentration below lethal threshold.

MDR significantly limits the efficacy of many cancer chemotherapy regimens and is a major factor in their failure. MDR may account for intrinsic resistance in colorectal and renal cancer, and for acquired resistance observed in acute non-lymphocytic leukemia, malignant lymphomas, myeloma, and breast and ovarian carcinomas.

Efforts to counter MDR have primarily involved the use of hydrophobic competitors for P-glycoprotein binding. U.S. Pat. No. 6,605,638 discloses a method for inhibiting P-glycoprotein activity by contacting cells with branched fatty acid (BFAs) and their derivatives. Most of these competitors eventually fail to overcome MDR due to their interference with chemotherapeutic drug uptake and unexpected toxicities. As a consequence, anticipated benefits of these agents are often unattainable or unrealized.

Amino Acids and Proliferative Disease

Asparagine is an essential amino acid that is required by rapidly proliferating cells. Mammalian cells can synthesize asparagine from aspartate using the ATP-dependent enzyme asparagine synthetase (CE 6.3.5.4), which transfers the amino group from the amide of glutamine to the β-carboxyl of aspartate in a reaction that may be represented as: Glutamine+Aspartate+ATP+$H_2O$=Glutamate+Asparagine+AMP+PPi.

Asparagine synthetase deficiency occurs in certain tumors, causing them to rely on an external supply of asparagine from other sources, such as serum. This observation led to the development of the enzyme L-asparaginase (type CE-2, CE 3.5.1.1) as a chemotherapeutic agent. L-asparaginase hydrolyzes L-asparagine to aspartate and ammonia, hence depleting L-asparagine from the serum and inhibiting tumor growth. L-asparaginase is used mainly in the treatment of Acute Lymphoblastic Leukemia (ALL) and shows some activity against other hematological cancers including acute non-lymphocytic leukemia (Whitecar, et al., 1970; Capizzi et al., 1970).

The L-asparaginase used in the clinic is available in two unmodified forms (native) purified from bacterial sources, and one as a PEGylated compound. U.S. Pat. No. 4,179,337 teaches PEGylated L-asparaginase, wherein the enzyme is coupled to PEG having a molecular weight of about 500 to 20,000 daltons.

The in vivo down-regulation of asparagine synthetase may provide an efficient mechanism for inhibiting tumor growth. However, cells respond to amino acid deprivation by a concerted increase in asparagine synthetase mRNA, protein, and enzymatic activity that involves transcriptional control of the asparagine synthetase gene. (Hutson, et al., 1997).

A metabolic approach was initially used to inhibit the activity of asparagine synthetase by the generation of L-asparagine and L-aspartic acid analogs. Analogs including 5-carboxamido-4-amino-3-isoxazolidone (Stammer et al., 1978) and N-substituted sulfonamides and N'-substituted sulfonylhydrazides have been prepared as sulfur analogues of L-asparagine (Brynes S et al., 1978a; Brynes S et al., 1978b). U.S. Pat. No. 4,348,522 teaches the salt of PALA, N-phosphonacetyl-L-aspartic acid, which has been shown to exhibit anti-tumor activity and is presently in clinical trials as combination chemotherapy for colorectal and pancreatic cancers (Whitehead et al, 2004a, 2004b).

Arginine has also been shown to be required for the growth of some tumor cell lines, including certain breast cancer cell lines (Caso, et al., 2004).

Other examples of amino acid derivatives and amino acid conjugates include sulphur containing tyrosine analogs having potent anti-melanoma activity (Thomas et al, 1999; McLaughlin et al, 1988; Tandon, et al, 1998) and antiproliferative activity (Purro et al, 2003). A proline analog of melphanan (Mel-pro) was shown to be a prodrug susceptible to the action of the cytosolic imidodipeptidase prolidase, suggesting that prolidase targeting may serve as a potential strategy in pharmacotherapy of breast cancer (Chrzanowski et al., 2003).

The use of prodrugs to impart desired characteristics such as increased bioavailability or increased site-specificity is a recognized concept in the art of pharmaceutical development. For example, direct or indirect conjugation of a drug to an antibody creates a stable conjugate that can arrive at the target site with minimum dissociation of the drug. Drug targeting may be combined with a mechanism of selective release of the drug for maximal potency.

The art neither teaches nor suggests compounds comprising a drug covalently linked to an amino acid via a side chain with a functional group selected from an amino group, a carboxyl, a sulfhydryl, a hydroxyl, a halogen, and a nitro group, useful for targeting drugs to neoplastic cells.

U.S. Pat. No. 4,296,105 describes doxorubicin derivatives linked to an optionally substituted amino acid at the hydroxy group of the amino acid residue, which possess in vitro a higher antitumor activity and lower toxicity than doxorubicin.

U.S. Pat. No. 5,962,216 teaches tumor activated prodrugs, which are unable to enter the cell, until cleaved by a factor or factors secreted by a target cell.

U.S. Pat. No. 5,650,386 teaches compositions comprising at least one active agent, and at least one modified non-alpha amino acid or poly amino acid, which acts as a carrier of the active agent. The amino acid modification includes acylation or sulfonation of at least one free amine group.

U.S. Pat. Nos. 6,623,731; 6,428,780 and 6,344,213 teach non-covalent mixtures comprising modified amino acids as carriers for biologically active agents.

U.S. Pat. No. 5,106,951 discloses a conjugate comprising an aromatic drug non-covalently intercalated between two aromatic side chains on an oligopeptide, and an antibody or antibody fragment covalently attached to the oligopeptide for targeting to cancer cells. U.S. Pat. No. 6,617,306 teaches a carrier for the in vivo delivery of a therapeutic agent, the carrier and therapeutic agent linked by a disulfide bond. In that patent, the carrier comprises a polymer, and at least one thiol compound conjugated to the polymer, such that the thiol group of the thiol compound and the thiol group of the therapeutic agent form a disulfide bond.

International patent application publication WO 00/33888 teaches cleavable anti-tumor and anti-inflammatory compounds comprising a therapeutic agent capable of entering a target cell, an oligopeptide, a stabilizing group and an optional linker.

It is to be explicitly understood that the present invention excludes known covalently linked conjugates of therapeutic agents and diagnostic agents to amino acid residues, enzymes, growth factors, peptide ligands of receptors, antibodies, as exemplified for instance in U.S. Pat. Nos. 5,106, 951 and 4,401,592, among others.

There remains an unmet medical need for compounds and compositions capable of overcoming multi-drug resistance in tumors and of targeting tumors while obviating cytotoxic damage to normal tissues.

SUMMARY OF THE INVENTION

It is an object of the present invention to target drugs and imaging agents to malignant cells and preclude uptake of the drugs by normal cells. The present invention provides novel compounds comprising amino acids including asparagine or glutamine or derivatives or analogs thereof covalently linked to a drug, which exhibit enhanced uptake by neoplastic cells, pharmaceutical compositions comprising the compounds and methods of treating a subject in need thereof.

The compounds of the present invention comprise a residue of an amino acid such as asparagine or glutamine or an analog or derivative thereof covalently linked to at least one drug, thereby providing an amino acid-drug conjugate. The conjugate may serve as a delivery vehicle for a drug or prodrug in which the drug undergoes rapid uptake by cancer cells; for example those cells that lack asparagine synthetase and depend upon external uptake of asparagine or glutamine.

According to one aspect the present invention provides a compound having the general formula (I):

wherein,

A denotes the side chain of an amino acid, said side chain having a functional group selected from the group consisting of an amino group, a carboxyl, a sulfhydryl and a hydroxyl;

D denotes an imaging agent carrier or the residue of a drug selected from the group consisting of a cytotoxic agent, a cytostatic agent and a chemotherapeutic agent;

$R^1$ and $R^2$ are independently selected from a group consisting of hydrogen, a lower alkyl, an amino acid, a peptide of about 2 to about 50 amino acids, a $C_1$-$C_{20}$ fatty acid, a sugar moiety, a polymer chain and a group of the formula:

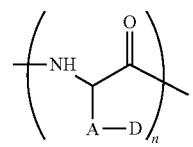

wherein n is an integer of 1-20;

$R^3$ is selected from H and a lower alkyl; and

X is selected from the group consisting of a carboxyl, an amide, a hydrazide, an ester, a thioester, an aldehyde, an amino acid and a peptide.

According to one embodiment, the amino acid side chain, A, derives from an amino acid or a derivative thereof selected from the group consisting of arginine, asparagine, aspartic acid, citrulline, cysteine, glutamic acid, glutamine, lysine, ornithine, serine, threonine, tryptophan, tyrosine, alpha-aminosuberic acid, 3,5-diiodotyrosine, homocitrulline, homoserine, hydroxyproline, penicillamine, statine, 4-ethylamine phenylglycine, 4-aminophenylglycine, 4-sulfophenylalanine, 4-aminophenylalanine and 2-amino-4[4-(2-amino)-pyrimidinyl]butanoic acid.

According to one specific embodiment the amino acid is selected from the group consisting of asparagine, aspartic acid, glutamic acid, glutamine, lysine and cysteine.

According to certain embodiments D is a drug selected from a group consisting of an alkaloid, an alkylating agent, an antibiotic, an antimetabolite, a DNA binding agent, a microtubule binding drug, a toxin and a DNA antagonist. The drug preferably provides cytostatic, cytotoxic and/or anti-proliferative activity. In certain embodiments the antimetabolite is selected from azacitidine, hydroxyurea, urethan and fluorouracil. In specific embodiments the drug is fluorouracil.

In specific embodiments the compound comprises an asparagine residue conjugated to a toxin selected from a group consisting of plant toxin, a microbial toxin and a snake venom toxin. In specific embodiments the toxin is selected from ricin, botulinum toxin, pseudomonas exotoxin, anthrax toxin, and diphtheria toxin.

In one embodiment $R^1$ and $R^2$ are both hydrogen. In another embodiment $R^1$ is hydrogen and $R^2$ is a polymer chain selected from a natural polymer and a synthetic polymer. In certain embodiments the synthetic polymer is selected from polyethylene glycol (PEG), polylactic acid, poly-L-lactic acid, poly-D,L-lactic acid, polyglycolic acid, poly-e-caprolactone, poly-p-dioxanon, tri-methylene carbonate, poly anhydrides, polyortho ester, polyurethanes, polyamino acids, poly(hydroxy alkanoates), polyphosphazenes and poly-beta-maleic acid. In certain embodiments $R^1$ and $R^2$ are polymer chains.

In other embodiments the natural polymer is selected from a protein and a polysaccharide. In certain embodiments the protein is selected from collagen, gelatin, laminin, keratin, albumin, fibronectin, fibrin and fibrinogen. In other embodiments the polysaccharide is selected from chitin, chitosan, alginate and sulfated polysaccharides including heparin, hyaluronic acid, heparan sulfate and chondroitin sulfate.

In specific embodiments, $R^1$ and $R^2$ are H and D is a metal chelator selected from the group consisting of DOTA and DTPA.

According to one embodiment X is a hydroxyl group. In other embodiments X is selected from the group consisting of an amide, a hydrazide, an ester, a thioester, an aldehyde, an amino acid and a peptide.

According to one specific embodiment an ester is selected from a group consisting of methyl-ester, ethyl-ester, propyl-ester, isopropyl-ester, butyl-ester, isobutyl-ester, tertbutyl-ester, tertpentyl-ester, 1-pentyl-ester, 2-pentyl-ester, 3-pentyl-ester, n-hexyl-ester, n-heptyl-ester, 2-heptyl-ester, 1-octyl-ester, 2-octyl-ester, n-nonyl-ester, n-decyl-ester, 1-dodecyl-ester, 1-myristyl-ester, cetyl-ester, stearyl-ester, and the like.

According to another embodiment a thioester modification of the carboxylic acid group of the amino acid residue is a derivative of thiol and is selected from a group consisting of methyl-mercapto-ester, ethyl-mercapto-ester, n-butyl-mercapto-ester, 2-butyl-mercapto-ester, tert-butyl-mercapto-ester, n-amyl-mercapto-ester, and the like.

According to one embodiment X is an amide group selected from the group consisting of a carboxy amide and a phosphono amide.

According to one embodiment the compound of the invention is a compound selected from a group consisting of compounds having general formula II and general formula III:

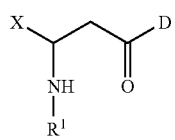

(II)

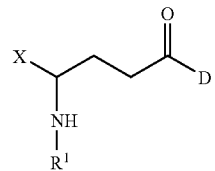

(III)

wherein,
D denotes an imaging agent carrier or the residue of a drug selected from the group consisting of a cytotoxic agent, a cytostatic agent and a chemotherapeutic agent;
$R^1$ is selected from a group consisting of hydrogen, a lower alkyl, an amino acid, a peptide of about 2 to about 50 amino acids, a $C_1$-$C_{20}$ fatty acid, a sugar moiety, a polymer chain and a group of the formula:

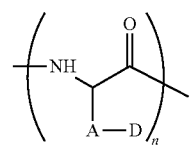

wherein n is an integer of 1-20; and
X is selected from the group consisting of a carboxyl, an amide, a hydrazide, an ester, a thioester, an aldehyde, an amino acid and a peptide.

In specific embodiments, the compound of the invention is L-aspartic acid-beta-1N-(2,4-dioxo-5-fluoropyrimidine; Asp (5-FU)), having chemical formula IV:

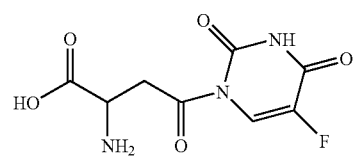

(IV)

In additional specific embodiments the compound of the invention is L-aspartamide-beta-1N-(2,4-dioxo-5-fluoropyrimidine), having chemical formula V:

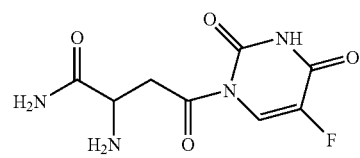

(V)

Another aspect of the present invention is directed to pharmaceutical compositions comprising as an active ingredient a compound selected from a group consisting of compounds having general formula (I), formula (II) and formula (III), and a pharmacologically acceptable carrier, excipient or diluent.

In another aspect the present invention relates to a method of treating a disorder comprising administering to a subject in need thereof a therapeutically effective amount of a compound selected from a group consisting of compounds having general formula (I), formula (II) and formula (III).

In certain embodiments a disorder includes any type of cancer including solid tumors and non-solid tumors. In specific embodiments the solid tumors are selected from tumors in the CNS (central nervous system), liver cancer, colorectal carcinoma, breast cancer, gastric cancer, pancreatic cancer, bladder carcinoma, cervical carcinoma, head and neck tumors, vulvar cancer and dermatological neoplasms including melanoma, squamous cell carcinoma and basal cell carcinomas. In other embodiment, non-solid tumors include lymphoproliferative disorders including leukemias and lymphomas. In other embodiments a disorder is metastatic disease.

The present invention further provides a method of treating cancer and metastases comprising contacting neoplastic cells with a therapeutically effective amount of an anti-cancer novel drug compound of the general formula (I). Thus, the invention comprises administration of the novel compound in concentration calculated to provide the subject being treated with appropriate milieu to provide prevention, control or cessation of cancer. In certain the embodiments the method of treating cancer comprises contacting neoplastic cells with a therapeutically effective amount of an anti-cancer novel drug compound of the general formula (II) or general formula (III). In specific embodiments the method of treating cancer comprises contacting neoplastic cells with a therapeutically effective amount of an anti-cancer novel drug compound of the general formula (IV). In other embodiments the method of treating cancer comprises contacting neoplastic cells with a therapeutically effective amount of an anti-cancer novel drug compound of the general formula (V).

In another aspect, the present invention provides a method for imaging a tumor in mammalian tissue comprising administering to the mammal an amount of a compound of formula (I) wherein D is an imaging agent carrier and detecting said compound. In certain embodiments the mammal is a human. In specific embodiments the mammalian tissue is located in the breast, lung, thyroid, lymph node, genitourinary system, musculoskeletal system, gastrointestinal tract, central or peripheral nervous system, head, neck, or heart.

In yet another aspect the present invention provides a method for treating a tumor in a mammal comprising administering to the mammal an effective therapeutic amount of a compound of formula (I) wherein D is an imaging agent carrier and wherein said compound comprises at least one therapeutic radionuclide. In specific embodiments the mammalian tissue is located in the breast, lung, thyroid, lymph node, genitourinary system, musculoskeletal system, gastrointestinal tract, central or peripheral nervous system, head, neck, or heart.

In yet another aspect the present invention provides a compound selected from a group consisting of compounds having general formula (I), formula (II) and formula (III) for use in medical therapy or diagnosis.

In certain embodiments of the present invention the imaging agent carrier is a metal chelator selected from DOTA and DTPA. In specific embodiments the compound of the present invention comprises at least one non-metallic or metallic radionuclide.

The present invention further provides a method of increasing the uptake of an anti-proliferative agent by neoplastic cells comprising contacting the neoplastic cells with an anti-proliferative compound general formula (I).

In another aspect the present invention further provides a method of overcoming multi-drug resistance in neoplastic cells comprising contacting the neoplastic cells with an anti-proliferative a compound selected from a compound having general formula (I).

The present invention further provides the use of a compound according to the invention for the preparation of a medicament for the treatment of cancer.
These And Other Embodiments Of The Present Invention Will Become Apparent In Conjunction With The Figures, Description And Claims That Follow.

DETAILED DESCRIPTION OF THE INVENTION

Figure 1:
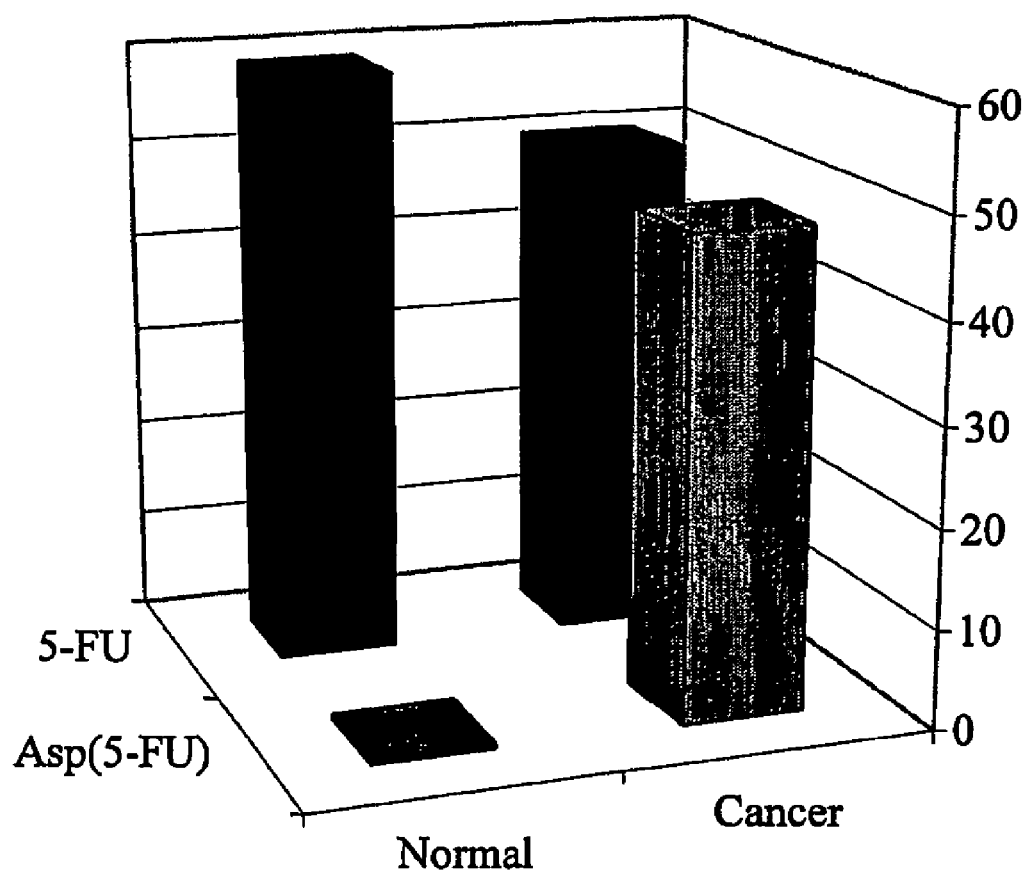
FIG. 1 provides the IC50 toxicity profiles of Asp(5-FU) versus 5-FU in normal and malignant cells in culture.

The present invention provides novel compounds comprising conjugates of amino acid or derivatives thereof covalently linked to therapeutic or diagnostic agents.

Conjugates

The conjugates of the present invention demonstrate enhanced uptake by proliferating cells such as neoplastic cells, yet exhibit limited uptake and reduced toxicity to normal cells.

The present invention provides a compound represented by general formula (I):

wherein,

A denotes the side chain of an amino acid, said side chain having a functional group selected from the group consisting of an amino group, a carboxyl, a sulfhydryl and a hydroxyl;

D denotes an imaging agent carrier or the residue of a drug selected from the group consisting of a cytotoxic agent, a cytostatic agent and a chemotherapeutic agent;

$R^1$ and $R^2$ are independently selected from a group consisting of hydrogen, a lower alkyl, an amino acid, a peptide of about 2 to about 50 amino acids, a $C_1$-$C_{20}$ fatty acid, a sugar moiety, a polymer chain and a group of the formula:

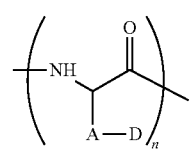

wherein n is an integer of 1-20;
R³ is selected from H and a lower alkyl; and
X is selected from the group consisting of a carboxyl, an amide, a hydrazide, an ester, a thioester, an aldehyde, an amino acid and a peptide.

In its broadest form, the present invention is directed to compounds having a formula as follows:

Z-A(D)-X wherein,

A denotes the residue of an amino acid or an amino acid derivative or analog selected from the group consisting of amino acids having a side chain with a functional group selected from an amino group, a carboxyl, a sulfhydryl, a hydroxyl, a halogen, and a nitro group;

D denotes an imaging agent carrier or the residue of a drug selected from the group consisting of a cytotoxic agent, a cytostatic agent and a chemotherapeutic agent;

D is covalently linked to A through said side chain functional group;

Z denotes one or two hydrogen atoms or one or two chemical derivatives at the amino group of the amino acid A, said derivative selected from an amino acid, a peptide of about 2 to about 50 amino acids, a $C_1$-$C_{20}$ fatty acid, a sugar moiety a polymer chain and a group of the formula

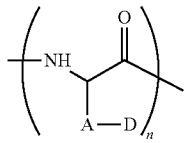

wherein n is an integer of 1-20; and

X denotes a carboxyl group or a chemical derivative at the carboxylic group of the amino acid A, said derivative selected from an amide group, a hydrazide, an ester, a thioester, an aldehyde, an amino acid and a peptide.

Embodiments of the Present Invention

According to one embodiment, the compounds of the present invention comprise the amino acid selected from the group consisting of arginine, asparagine, aspartic acid, citrulline, cysteine, glutamic acid, glutamine, lysine, ornithine, serine, threonine, tryptophan, tyrosine, alpha-aminosuberic acid, 3,5-diiodotyrosine, homocitrulline, homoserine, hydroxyproline, penicillamine, statine, 4-ethylamine phenylglycine, 4-aminophenylglycine, 4-sulfophenylalanine, 4-aminophenylalanine and 2-amino-4[4-(2-amino)-pyrimidinyl]butanoic acid.

According to specific embodiments the amino acid is selected from the group consisting of asparagine, aspartic acid, glutamic acid, glutamine, lysine and cysteine.

Without wishing to be bound to theory, the amino-acid conjugates of the present invention are transported into the cell via amino acid transporters thereby bypassing multi-drug resistance (MDR) mechanisms, and arrest cell growth or kill the cell from within.

The present invention also relates to an asparagine-drug conjugate wherein the drug is a toxin, which can inhibit enzymes involved in the metabolism of asparagine. One important enzyme that can be inhibited by the asparagine-toxin conjugate is asparagine synthetase, which is essential for asparagine synthesis in mammalian cells. Other enzymes involved in the metabolism of glycoproteins, especially those that have N-linked sugars connected to the asparagine amino acid in the protein including, but not limited, glucosidase I, glucosidase II, calnexin, and alpha-glucosyltransferase can be potentially inhibited by an asparagine-toxin conjugate. N-glycosylation in N-glycan proteins occurs on asparagine at the consensus sequence Asn-X-Ser/Thr, and interference with glycosylation metabolism disrupts the folding and secretion of glycoproteins. Inhibition of glycosylation of essential glycoproteins will cause cell arrest and cell death.

An asparagine-toxin conjugate can also affect the metabolism of other amino acids such as ornithine, since asparagine has been shown to be involved in membrane Na+/H+ antiport in ornithine decarboxylase induction (Fong and Law, 1988).

Asparagine-toxin can undergo fast uptake by aspartate and glutamate transporters, which mediate transmission of glutamic/glutamine and aspartic/asparagine amino acids through the blood brain barrier (BBB), and can be applied as efficient drug delivery system to transport chemotherapeutic drugs to treat tumors of the CNS. It has been shown that cerebrospinal fluid (CSF) and plasma levels of asparagine are significantly lower in patients with primary and secondary tumors of the Central Nervous System (CNS), (Piek et al., 1987).

Hepatoma cancer cells have been shown to express a new glutamine transporter (McGivan, 1998), which show a much higher rate of glutamine uptake in human hepatoma cells, and not in normal hepatocytes, thus indicating that glutamine-toxin can be used for treatment of liver cancers.

Another therapeutic application of asparagine and glutamine analogs as conjugates to pyrimidine and purine antagonists, including floxuridine, is disclosed U.S. Pat. Nos. 2,949,451 and 3,041,335. The pharmaceutical composition described has a dual function: as an antineoplastic and as an antiviral agent. Potential asparagine and glutamine drug conjugates useful for antiviral treatment include acyclovir, cidofovir, cytarabin, dideoxyadenosine, didanosine, edoxudine, famcicolovir, floxuridine, ganciclovir, idoxuridine, inosine pranobex, lamivudine, MADU, penciclovir, sorivudine, stavudin, trifluridine, valacyclovir, vidarabine, zalcitabine, zidovudine.

Toxins which may be particularly useful for conjugating to an amino acid or derivative thereof include plant toxins, microbial toxins and snake venom toxins. In specific embodiments the toxin is selected from ricin, botulinum toxin, pseudomonas exotoxin, anthrax toxin, and diphtheria toxin.

DEFINITIONS

For convenience and clarity certain terms employed in the specification, examples and claims are described herein.

The term "residue of a drug" refers to a drug excluding the functional group that that was used to attach the amino acid in forming the amino acid-drug conjugate A(D).

The term "drug" denotes any pharmacologically active agent capable of arresting cell growth, or inducing death of the hyperproliferative cell or labeling a cell in which it is present and includes known cytotoxic, cytostatic, antiproliferative drugs, or imaging agents such as are known in the art, exemplified by the following compounds:

Alkaloids including docetaxel, etoposide, irinotecan, paclitaxel (Taxol), teniposide, topotecan, vinblastine, vincristine, vindesine.

Alkylating agents including busulfan, improsulfan, piposulfan, benzodepa, carboquone, meturedepa, uredepa, altretamine, triethylenemelamine, triethylenephosphoramide, triethylenethiophosphoramide, chlorambucil, chloranaphazine, cyclophosphamide, estramustine, ifosfamide, mechlorethamine, mechlorethamine oxide HCl, melphalan novembichin, perfosfamide phenesterine, prednimustine, trofosfamide, uracil mustard, carmustine, chlorozotocin, fotemustine, lomustine, nimustine, semustine ranimustine, dacarbazine, mannomustine, mitobronitol, mitolactol, pipobroman, temozolomide.

Antibiotics and analogs thereof including aclacinomycins, actinomycins, anthramycin, azaserine, bleomycins, cactinomycin, carubicin, carzinophilin, cromomycins, dactinomycins, daunorubicin, 6-diazo-5-oxo-1-norleucine, doxorubicin, epirubicin, idarubicin, menogaril, mitomycins, mycophenolic acid, nogalamycine, olivomycins, peplomycin, pirarubicin, plicamycin, porfiromycin, puromycine, streptonigrin, streptozocin, tubercidin, zinostatin, zorubicin.

Antimetabolites including denopterin, edatrexate, mercaptopurine (6-MP), methotrexate, piritrexim, pteropterin, pentostatin (2'-DCF), tomudex, trimetrexate, cladridine, fludarabine, thiamiprine, ancitabine, azacitidine, 6-azauridine, carmofur, cytarabine, doxifluridine, emitefur, floxuridine, fluorouracil, gemcitabine, tegafur, hydroxyurea and urethan;

Platinum complexes including caroplatin, cisplatin, miboplatin, oxaliplatin;

Microtubule binding agents including vinblastine and taxol;

Other drugs including aceglatone, amsacrine, bisantrene, defosfamide, demecolcine, diaziquone, eflornithine, elliptinium acetate, etoglucid, etoposide, fenretinide, gallium nitrate, hydroxyurea, lonidamine, miltefosine, mitoguazone, mitoxantrone, mopidamol, nitracrine, pentostatin, phenamet, podophillinic acid 2-ethyl-hydrazide, procarbazine, razoxane, sobuzoxane, spirogermanium, teniposide tenuazonic acid, triaziquone, 2,2',2"-trichlorotriethylamine; and Pyrimidine and purine antagonists including fluorouracil (5-FU), fluorodeoxyuridine (5-FUDR), azacytidine (5-AZC), 6-thioguanine (6-TG), chlorodeoxyadenosine (2-CDA).

The classification of drugs herein is made for the sake of convenience only and is not intended to limit any component to a particular application or applications listed.

As used herein, "arresting cell growth" and "inducing death" of the hyperproliferative cell, e.g., neoplastic cell, refers to slowing, interrupting, arresting or stopping its growth and metastasis, and does not necessarily indicate a total elimination of the neoplastic growth.

The amino acids used in this invention are those, which are available commercially or are available by routine synthetic methods. Natural coded amino acids and their derivatives are represented by three-letter codes according to IUPAC conventions. When there is no indication, either the L or the D isomer may be used. The D isomers are indicated by "D" before the residue abbreviation.

In the conjugate according to the present invention, the drug is covalently attached to the side chain of the amino acid or amino acid analog. The skilled artisan will be able to optimize the appropriate linkage and position of the drug moiety within the compound. Various concerns should be taken into consideration to guide the artisan in this decision, such as selection of the specific drug, selection of the derivatives, selection of the position of attachment to the drug species, and requirements concerning host intracellular enzymes for drug activation.

According to the present invention, in those embodiments where R comprises a peptide, the size of the peptide about 2 to about 50 amino acids, preferably fewer than 40 amino acids, more preferably fewer than about 30 amino acids and most preferably fewer than about 20 amino acids.

The term "alkyl" is intended to include linear, branched, or cyclic hydrocarbon structures and combinations thereof "Lower alkyl" refers to linear, branched or cyclic alkyl groups of from 1 to 6 carbon atoms. Examples of lower alkyl groups include but are not limited to methyl, ethyl, propyl, isopropyl, butyl, s- and t-butyl and the like. Cycloalkyl is a subset of alkyl and includes cyclic hydrocarbon groups of from 3 to 6 carbon atoms. Examples of cycloalkyl groups include cyclopropyl, cyclobutyl, cyclopentyl, cyclohexyl and the like.

It is to be explicitly understood that the present invention does not encompass drug or imaging agent conjugates known in the art, specifically excluded are known drug conjugates to amino acid residues enzymes, growth factors, peptide ligands of receptors, antibodies as exemplified for instance in U.S. Pat. Nos. 5,106,951, 4,859,764 and 4,401,592, among many others.

The principles that apply to the selection of peptide, linker, attachment site, etc., will be detailed herein for exemplary compounds. The principles may be generalized as follows:

a) Selection of the amino acid or amino acid derivative or analog: aspartate/asparagine and glutamate/glutamine and any of their derivatives or analogs that can undergo rapid uptake by cancer cells are suitable, as is lysine and cysteine;

b) Selection of the carboxy terminal compounds: a chemical moiety that can serve as a carrier;

c) Selection of the amino terminal compounds: the groups may be selected from any chemical moiety that reduces the non-specific compound degradation and augments its stability;

d) selection of D: D denotes an imaging agent carrier or the residue of a drug selected from the group consisting of a cytotoxic agent, a cytostatic agent and a chemotherapeutic agent;

e) Selection of the drug: the drug can be selected from anti-proliferative agents, cytotoxic agents, cytostatic agents, and salts and derivatives thereof.

The compounds described herein comprise an anti-cancer drug or an imaging agent conjugated to an amino acid or derivatives or analogs of amino acids. The compounds of the present invention can be readily prepared from amino acids by methods familiar to one with skill in the art. The methods include, in a non-limiting manner, methods described in International patent application publications WO96/30036 and WO97/36480, and U.S. Pat. Nos. 5,643,957 and 5,650,386, among others. For example, the compounds may be prepared by reacting the single amino acid with the appropriate acylating or amine-modifying agent, which reacts with a free amino moiety present in the amino acid to form amides. Protecting groups may be used to avoid unwanted side reactions as would be known to those skilled in the art.

Toxicity and therapeutic efficacy of the peptides described herein can be determined by standard pharmaceutical procedures in cell cultures or experimental animals, e. g., by determining the IC50 (the concentration which provides 50% inhibition) and the LD50 (lethal dose causing death in 50% of the tested animals) for a subject compound. The data obtained from cell culture assays and animal studies can be used in formulating a range of dosage for use in human subjects. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 pp. 1).

The amount of active agent used in a composition of the present invention is an amount effective to accomplish the purpose of the particular active agent for the target indication. The amount of active agent in the compositions typically is a pharmacologically, biologically, therapeutically, or chemically effective amount. However, the amount can be less than that amount when the composition is used in a dosage unit form because the dosage unit form may contain a plurality of compounds or active agents in a single composition or may contain a divided pharmacologically, biologically, therapeutically, or chemically effective amount. The total effective amount can then be administered in cumulative units containing, in total, an effective amount of the active agent.

The pharmaceutical compositions of the present invention comprise at least one of the compounds of the present invention, and one or more pharmaceutically acceptable excipients or diluents.

This invention includes the hydrates and the pharmaceutically acceptable salts of the compounds of general formula (I). A compound of this invention can possess a sufficiently basic functional group which can react with any of a number of inorganic and organic acids, to form a pharmaceutically acceptable salt.

The term "pharmaceutically acceptable salt" as used herein, refers to salts of the compounds of the general formula (I), formula (II) and formula (III), which are substantially non-toxic to living organisms. Typical pharmaceutically acceptable salts include those salts prepared by reaction of the compounds of the present invention with a pharmaceutically acceptable mineral or organic acid. Such salts are also known as acid addition salts.

As used herein, the term "stereoisomer" refers to a compound made up of the same atoms bonded by the same bonds but having different three-dimensional structures, which are not interchangeable. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers, which are not enantiomers. In addition, two diastereomers, which have a different configuration at only one chiral center are referred to herein as "epimers". The terms "racemate", "racemic mixture" or "racemic modification" refer to a mixture of equal parts of enantiomers. The present invention includes enantiomers of the compounds having general formula (I), (II) and (III), and the specific compounds described herein.

Pharmaceutical Compositions

The present invention further provides pharmaceutical compositions comprising the compounds described herein as active agents.

The compositions comprising the compounds of the present invention have utility in the delivery of active agents to selected biological systems and in an increased or improved bioavailability of the active agent compared to administration of the active agent without the delivery agent. Delivery can be improved by delivering more active agent over a period of time, or in delivering active agent in a particular time period (such as to effect quicker or delayed delivery) or over a period of time (such as sustained delivery).

Pharmaceutical compositions of the present invention may be manufactured by processes well known in the art, e.g., by means of conventional mixing, dissolving, granulating, grinding, pulverizing, dragee-making, levigating, emulsifying, encapsulating, entrapping or lyophilizing processes.

As used herein a "pharmaceutical composition" refers to a preparation of one or more of the compounds described herein, or physiologically acceptable salts or solvents thereof, with other chemical components such as physiologically suitable carriers and excipients. The purpose of a pharmaceutical composition is to facilitate administration of a compound to a subject.

Pharmaceutical compositions for use in accordance with the present invention thus may be formulated in conventional manner using one or more physiologically acceptable carriers comprising excipients and auxiliaries, which facilitate processing of the active compounds into preparations which, can be used pharmaceutically. Proper formulation is dependent upon the route of administration chosen.

For injection, the compounds of the invention may be formulated in aqueous solutions, preferably in physiologically compatible buffers such as Hank's or Ringer's solution or physiological saline buffer. For transmucosal and transdermal administration, penetrants appropriate to the barrier to be permeated may be used in the formulation. Such penetrants, including for example DMSO or polyethylene glycol, are known in the art.

For oral administration, the compounds can be formulated readily by combining the active compounds with pharmaceutically acceptable carriers well known in the art Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethyl-cellulose; and/or physiologically acceptable polymers such as polyvinylpyrrolidone (PVP). If desired, disintegrating agents may be added, such as cross-linked polyvinyl pyrrolidone, agar or alginic acid or a salt thereof such as sodium alginate.

In addition, enterocoating is useful as it is desirable to prevent exposure of the peptides of the invention to the gastric environment.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers.

In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by inhalation, the peptides for use according to the present invention are conveniently delivered in the form of an aerosol spray presentation from a pressurized pack or a nebulizer with the use of a suitable propellant, e. g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e. g., gelatin for use in an inhaler or insufflator may be formulated containing a powder mix of the peptide and a suitable powder base such as lactose or starch.

Pharmaceutical compositions for parenteral administration include aqueous solutions of the active ingredients in water-soluble form. Additionally, suspensions of the active compounds may be prepared as appropriate oily injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents, which increase the solubility of the compounds, to allow for the preparation of highly concentrated solutions.

The compounds of the present invention may also be formulated in rectal compositions such as suppositories or retention enemas, using, e.g., conventional suppository bases such as cocoa butter or other glycerides.

Depending on the severity and responsiveness of the condition to be treated, dosing can also be a single administration of a slow release composition, with course of treatment lasting from several days to several weeks or until cure is effected or diminution of the disease state is achieved. The amount of a composition to be administered will, of course, be dependent on many factors including the subject being treated, the severity of the affliction, the manner of administration, the judgment of the prescribing physician.

Diagnostics and Imaging

The present invention further provides the compounds as described herein for the diagnosis, imaging and treatment of tumors. The compound of the present invention preferably has a high uptake in tumor cells but low non-specific uptake in normal tissues.

The term "imaging agent" denotes a labeled compound that is detectable using imaging equipment. Such label can be radioactive, fluorescent, calorimetric, or magnetic. The imaging agent preferably comprises a label selected from a metallic or non-metallic isotope. The imaging agent is capable of detecting cancer or other neoplastic cells in diagnostic procedures in vivo or in vitro.

As used herein, an "imaging agent carrier" is a moiety capable of binding the detectable label. According to certain embodiments the imaging agent carrier is a chelating group capable of chelating at least one detectable isotope (e.g., a metallic radioisotope) that serves as a marker of cancer or other neoplastic cells in a diagnostic procedure in vivo or in vitro. Any suitable chelating group can be employed. Specifically, the chelating group can be selected from NTA, HEDTA, DCTA, RP414, MDP, DOTATOC, CDTA, HYNIC, EDTA, DTPA, TETA, DOTA, DOTMP, DCTA, 15N4, 9N3, 12N3, or MAG3. Other examples of chelators include ethylenediamine, propylenediamine, diethylenetriamine, triethylenetetraamine, ethylenediaminetetraaceto, oxalato, hydroxyquinolates, hydroxyqinones, aminoquinones, dipyridyl, phenanthroline, acetylacetone, oxalic acid and bifunctional acids. In specific embodiments the chelating group is selected from DOTA (1,4,7,10-tetraazacyclododecan-1,4,7,10-tetraacetic acid) and DTPA (diethylene-triaminopentaacetic acid). In one embodiment, the imaging agent carrier further comprises at least one radionuclide as defined herein.

As used herein, a "detectable radionuclide" is any suitable radionuclide (i.e., radioisotope) capable of detecting cancer or other neoplastic cells in a diagnostic procedure in vivo or in vitro. Suitable detectable radionuclides include metallic and non-metallic radionuclides.

The non-metallic radionuclide can be a paramagnetic atom (e.g., Fluorine-19) or a non-metallic positron emitting radionuclide (e.g., Carbon-11, Fluorine-18, Iodine-123, or Bromine-76). The metallic radionuclide can be a diagnostic gamma emitter (e.g., Tc-99m, In-111, Iodine-131, or Iron-59); a diagnostic metallic positron emitting radionuclide (e.g., Bismuth-206, Bismuth-207, Cobalt-55, Gallium-64, Copper-67, Yttrium-86, or Yttrium-88); or a paramagnetic diagnosis metal ion (e.g., Europium-152 or Gadolinium-157).

As used herein, a "therapeutic radionuclide" is any suitable radionuclide (i.e., radioisotope) that possesses therapeutic efficacy against cancer or other neoplastic cells in vivo or in vitro. Suitable therapeutic radionuclides include metallic radionuclides including Actinium-223, Bismuth-212, Indium-111, Rhenium-186, Rhenium-188, Strontium-89, Tin-117m, and Yttrium-90 or a therapeutic paramagnetic metal ion (e.g., Gadolinium-157).

The term "metal chelator" refers to a chemical species (molecule, compound) having at least one coordinating group which is able to form a complex (coordinate) with a metal ion.

In a non-limiting example, suitable non-metallic radionuclides include Carbon-11, Fluorine-18, Bromine-76, or Iodine-123, and Iodine-124 and metallic radionuclides include Antimony-124, Antimony-125, Arsenic-74, Barium-103, Barium-140, Beryllium-7, Bismuth-206, Bismuth-207, Cadmium-109, Cadmium-115m, Calcium-45, Cerium-139, Cerium-141, Cerium-144, Cesium-137, Chromium-51, Cobalt-55, Cobalt-56, Cobalt-57, Cobalt-58, Cobalt-60, Cobalt-64, Copper-67, Erbium-169, Europium-152, Gallium-64, Gallium-68, Gadolinium-153, Gadolinium-157, Gold-195, Gold-199, Hafnium-175, Hafnium-175-181, Holmium-166, Indium-110, Indium-111, Iridium-192, Iron-55, Iron-59, Krypton-85, Lead-210, Manganese-54, Mercury-197, Mercury-203, Molybdenum-99, Neodymium-147, Neptunium-237, Nickel-63, Niobium-95, Osmium-185+191, Palladium-103, Platinum-195m, Praseodymium-143, Promethium-147, Protactinium-233, Radium-226, Rhenium-186, Rhenium-188, Rubidium-86, Ruthenium-103, Ruthenium-106, Scandium-44, Scandium-6, Selenium-75, Silver-110m, Silver-111, Sodium-22, Strontium-85, Strontium-89, Strontium-90, Sulfur-35, Tantalum-182, Technetium-99m, Tellurium-125, Tellurium-132, Thallium-204, Thorium-228, Thorium-232, Thallium-170, Tin-113, Tin-114, Tin-117m, Titanium-44, Tungsten-185, Vanadium-48, Vanadium-49, Ytterbium-169, Yttrium-86, Yttrium-88, Yttrium-90, Yttrium-91, Zinc-65, and Zirconium-95. In certain embodiments the radionuclide is selected from for example Technetium-99m, Thalium-201, Indium-111, Gallium-67, Yttrium-90, Lutetium-177 and Iodine-123.

EXAMPLES

The following examples are to be considered merely as illustrative and non-limiting in nature. It will be apparent to one skilled in the art to which the present invention pertains that many modifications, permutations, and variations may be made without departing from the scope of the invention.

The following abbreviations are used in the Examples:
5-FU: 2,4-dioxo-5-fluoropyrimidine
BOC: t-butyloxycarbonyl
DCC: N,N'-dicyclohexylcarbodiimide
DCM: dichloromethane
DIC: diisopropyl carbodiimide
DIEA: diisopropylethylamine
DMAP: dimethyl aminopyridine
Fmoc: 9-fluorenylmethyloxycarbonyl
HBTU: 2-(1H-benzotriazole-1-yl)-1,1,3,3-tetramethyluronium hexafluorophosphate
HOBt: N-hydroxybenzotriazole
NMP: N-methyl 2-pyrrolidone
OtBu: t-butyl ester
TFA: trifluoroacetic acid

Example 1

Synthesis of L-aspartic acid-beta-1N-(2,4-dioxo-5-fluoropyrimidine) (formula IV)

One mmol of BOC-Asp-OtBu was dissolved in 20 ml DCM. The mixture was cooled to 0° C. 1.1 mmol of DCC was dissolved in 10 ml DCM and added to the BOC-Asp-OtBu mixture. The reaction was carried out for 30 minutes on cold ice and continued for another 2 hours at room temperature. The white crystals that appeared in the mixture were filtered out.

One mmol of solid 2,4-dioxo-5-fluoropyrimidine (5-FU) was added to the clear solution of activated BOC-Asp-OtBu. The reaction was carried out for 20 hours at room temperature. The mixture was filtered and the DCM was evaporated. The product was washed several times with water and ethanol and air-dried. Cleavage of the protecting groups (BOC, OtBu) was carried out in 1 ml TFA (trifluoroacetic acid)+5% water for 3 hours. The acid was evaporated in a vacuum over a KOH pellet. The final product was washed several times with diethyl ether and dried.

L-aspartic acid beta-1N-(2,4-dioxo-5-fluoropyrimidine) [Asp(5-FU)] was recrystallized from methanol. Yield of the product was 79% of white crystals, melting point 208° C. (decomposition). Molecular weight: 245 g/mol.

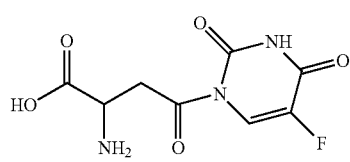

(IV)

Compound 1: Asp(5-FU) L-aspartic acid-beta-1N-(2,4-dioxo-5-fluoropyrimidine)

Example 2

Synthesis of L-aspartamide-beta-1N-(2,4-dioxo-5-fluoropyrimidine)(formula V)

1 mmol of BOC-Asp-NH2 was dissolved in 20 ml NMP (N-methyl 2-pyrrolidone). One mmol of HBTU, 1 mmol HOBt and 3 mmol of DIEA (Diisopropylethylamine) were added to BOC-Asp-NH2 solution and mixed for 20 minutes. 1 mmol of solid 2,4-dioxo-5-fluoropyrimidine was added to the solution of activated BOC-Asp-NH2. The reaction was carried out for 20 hours at room temperature. The mixture was filtered and the product was precipitated from NMP by ice-cold t-butyl methyl ether. The product was washed several times with ether and air-dried. Cleavage of the protecting group (BOC) was carried out in 1 ml TFA+5% water for 3 hours. The acid was evaporated in a vacuum over KOH pellet. The final product was washed several times with diethyl ether and dried.

L-aspartamide beta-1N-(2,4-dioxo-5-fluoropyrimidine) denoted herein formula V, was dissolved in methanol and precipitated with DCM. Yield of the product was 80% of white crystals. Molecular weight 244 g/mol.

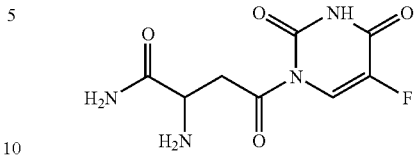

Compound 2—L-aspartamide-beta-1N-(2,4-dioxo-5-fluoropyrimidine)

Example 3

Synthesis of L-glutamic acid-beta-1N-(2,4-dioxo-5-fluoropyrimidine)

One mmol of BOC-Glu-OtBu was dissolved in 20 ml DCM (Dichloromethane). The mixture was cooled to 0° C. and 1.1 mmol of DCC was dissolved in 10 ml DCM and added to the BOC-Glu-OtBu mixture. The reaction was carried out for 30 minutes on cold ice and continued for another 2 hours at room temperature. The white crystals that appeared in the mixture were filtered out.

One mmol of solid 2,4-dioxo-5-fluoropyrimidine was added to the clear solution of activated BOC-Glu-OtBu. The reaction was carried out for 20 hours in room temperature. The mixture was filtered and the DCM was evaporated. The product was washed several times with water and ethanol and air-dried. Cleavage of the protecting groups (BOC, OtBu) was carried out in 1 ml TFA+5% water for 3 hours. The acid was evaporated in a vacuum over KOH pellet. The final product was washed several times with diethyl ether and dried.

L-glutamic acid beta-1N-(2,4-dioxo-5-fluoropyrimidine) (compound 3) was recrystallized from methanol. Yield of the product was 76% of white crystals. Molecular weight: 259 g/mol.

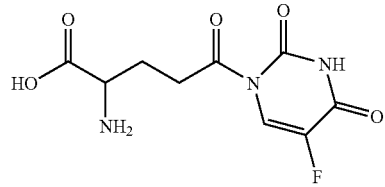

Compound 3: L-glutamic acid-beta-1N-(2,4-dioxo-5-fluoropyrimidine)

Example 4

Synthesis of L-glutamide-beta-1N-(2,4-dioxo-5-fluoropyrimidine)

One mmol of BOC-Glu-NH2 was dissolved in 20 ml NMP. One mmol of HBTU, 1 mmol HOBt and 3 mmol of DIEA were added to the BOC-Glu-NH2 solution and mixed for 20 minutes. 1 mmol of solid 2,4-dioxo-5-fluoropyrimidine was added to the activated BOC-Glu-NH2 solution. The reaction was carried out for 20 hours at room temperature. The mixture was filtered and the product was precipitated from NMP by ice-cold t-Butyl methyl ether. The product was washed several times with ether and air-dried. Cleavage of the protecting group (BOC) was carried out in 1 ml TFA and 5% water for 3 hours. The acid was evaporated in a vacuum over KOH pellet. The final product was washed several times with diethyl ether and dried.

L-glutamide beta-1N-(2,4-dioxo-5-fluoropyrimidine) (compound 4) was dissolved in methanol and precipitated with DCM. Yield of the product was 70% of white crystals. Molecular weight: 258 g/mol.

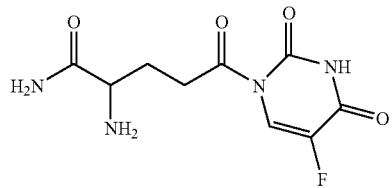

Compound 4:
L-glutamide-beta-1N-(2,4-dioxo-5-fluoropyrimidine)

Example 5

Synthesis of Hydroxyuroyl-beta-L-aspartic acid

A. Synthesis of hydroxyurea-O(Trt)

Two mmol of chlorotriphenylmethane is dissolved in 20 ml DCM+1% DMF. Two mmol of dry hydroxyurea is added to the reaction and mixed for 1 hour. Four mmol of triethylamine is added to the mixture with catalytic amount of DMAP. The reaction is mixed for 20 hours. The DCM is evaporated in a vacuum, and 10 ml of cold diethylether was added to precipitate the product. The precipitate was washed several times with ether, and recrystallized from ethanol. The product hydroxyurea—O(Trt) gave 50% yield, and molecular weight of 318 g/mol.

B. Synthesis of Hydroxyuroyl-beta-L-aspartic acid

One mmol of BOC-Asp-OtBu was dissolved in 20 ml DCM. The mixture was cooled to 0° C. 1.1 mmol of DCC was dissolved in 10 ml DCM and added to the BOC-Asp-OtBu mixture. The reaction was carried out as in example 1.

One mmol of solid hydroxyurea-O(Trt) was added to the clear solution of activated BOC-Asp-OtBu. The reaction was carried out for 20 hours in room temperature. The mixture was filtered and the DCM was evaporated. The product was washed several times with water and ethanol and air-dried. Cleavage of the protecting groups (BOC, OtBu, Trt) was carried out in 1 ml TFA/5% water for 3 hours. The acid was evaporated in a vacuum over KOH pellet. The final product was washed several times with diethyl ether and dried.

Hydroxyuroyl-beta-L-aspartic acid (compound 5) was recrystallized from ethanol. The product yield was 68%, with molecular weight of 191 g/mol.

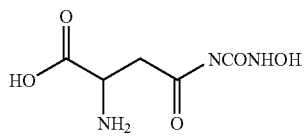

Compound 5: Hydroxyuroyl-beta-L-aspartic acid

Example 6

Synthesis of Urethan-beta-L-aspartic acid

2-Chlorotrityl chloride resin (100-200 mesh, 1% DVB), substitution of 1.2 g/mol was swollen in DCM for 1 hour. The resin was washed several times with DCM. 2.4 mmol of Fmoc-Asp(ODmab)-OH was dissolved in 20 ml DCM and added to the resin, 4.8 mmol of diethyl isopropylamine, was added to the reaction and the reaction was carried out for 2 hours at room temperature.

The resin was washed several times with DCM, methanol, DCM. ODmab protecting group was removed by washing the resin 7 times for 2 minutes each time with 2% hydrazine in DMF. The resin was washed several times with DMF and DCM followed by DMF. 2.4 mmol of urethan was dissolved in DMF, with 2.4 mmol DIC. The reaction was carried out for 2 hours at room temperature. The resin was washed several times with DMF and DCM, followed by DMF. Fmoc protecting group was removed by incubation in 20% piperidine in DMF 3 times for 10 minutes each time. The resin was washed several times with DMF, DCM. The resin was dried in a vacuum. The product was cleaved from the resin by 1 ml of 1% of TFA in DCM+1% water for 30 minutes. The acid/DCM was evaporated in a vacuum over KOH pellet. The final product was washed several times with diethyl ether and dried.

Urethan-beta—L-aspartic acid (compound 6) was recrystallized from ethanol. Yield of the product was 72%, with molecular weight of 204 g/mol.

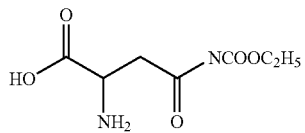

Compound 6: Urethan-beta-L-aspartic acid

Example 7

Synthesis of 6—Mercaptopurine-beta-L-Cysteine

One gram (1 g) Wang resin (100-200 mesh, 1% DVB), substitution of 0.8 g/mol was swollen in DMF for 1 hour. The resin was washed several times with DMF. 1.6 mmol of Fmoc-Cys(Mmt)-OH was dissolved in 10 ml DCM and added to the resin, 2.4 mmol of pyridine, and 1.6 mmol 2,6-dichlorobenzoyl chloride were added to the reaction. The reaction was carried out for 20 hours at room temperature.

The resin was washed several times with DCM, DCE. The remaining hydroxyl groups were blocked with 0.3 ml benzoyl chloride and 0.3 ml pyridine in 8 ml DCE for 2 hours. The resin was washed with DCE, DCM. Mmt protecting group was removed by washing the resin 7 times for 2 minutes each time with 0.5% TFA in DCM. The resin was washed several times with DCM, DMF. 0.8 mmol 6-Mercaptopurine was dissolved in 10 ml DMF and added to the resin with 8 mmol of dry I$_2$ (Iodine). The reaction was carried out for 5 hours at room temperature. The resin was washed several times with DMF and DCM, followed by DMF. Fmoc protecting group was removed by incubation in 20% piperidine in DMF 3 times for 10 minutes each time. The resin was washed several times with DMF, DCM. The resin was dried in a vacuum. The product was cleaved from the resin by 1 ml of 95% of TFA+ 5% water for 2 hours. The acid was evaporated in a vacuum over KOH pellet. The final product was washed several times with diethyl ether and dried.

6-mercaptopurine-beta-L-cysteine was recrystallized from methanol. Yield of the product was 38%, having molecular weight of 270 g/mol.

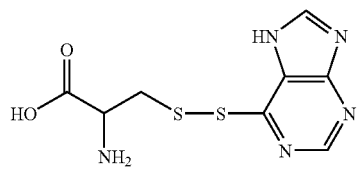

Compound 7: 6-mercaptopurine-beta-L-cysteine

Example 8

Synthesis of L-aspartate hydrazide-beta-1N-(2,4-dioxo-5-fluoropyrimidine) and derivatives on 4-hydroxymethylbenzoic acid (HMBA) resin One gram of HMBA resin (Sheppard et al., 1982), substitution of 0.7 g/mol was swollen in DCM for 1 hour. The resin was washed several times with DCM. 3.5 mmol of Fmoc-Asp (ODmab)-OH was dissolved in 20 ml DCM with 3.5 mmol DIC and 3.5 mmol HOBt mixed for 20 minutes and then added to the resin. The reaction was carried out for 2 hours at room temperature. The resin was washed several times with DCM, methanol, DCM. ODmab protecting group was removed by washing the resin 7 times for 2 minutes each time with 2% hydrazine in DMF. The resin was washed several times with DMF, DCM and then DMF.

1.4 mmol of 5-FU was dissolved in DMF, with 0.7 mmol DIC. The reaction was carried out for 2 hours at room temperature. The resin was washed several times with DMF, DCM, DMF. Fmoc protecting group was removed by incubation in 20% piperidine in DMF 3 times for 10 minutes each time. The resin was washed several times with DMF, DCM. The resin was dried in a vacuum. The resin was partitioned into 4 parts, each part was cleaved with a unique mix to yield the following products:

a. L-aspartate hydrazide-beta-1N-(2,4-dioxo-5-fluoropyrimidine) (Compound 8). The product was cleaved from the resin using 5 ml of 5% of Hydrazine in DMF for 1 hour. The final product was precipitated, and washed several times with diethyl ether and dried. L-aspartate hydrazide-beta-1N-(2,4-dioxo-5-fluoropyrimidine) is recrystallized from ethanol.

b. L-aspartate methyl ester-beta-1N-(2,4-dioxo-5-fluoropyrimidine) (Compound 9). The product was cleaved from the resin using 10 ml of mix DIEA/methanol/DMF (1:5:5) for 16 hours at 50° C. The eluate was evaporated by rotary evaporator. The product was precipitated, and washed several times with diethyl ether and dried. L-aspartate methyl ester-beta-1N-(2,4-dioxo-5-fluoropyrimidine) was recrystallized from methanol.

c. L-aspartate alcohol-beta-1N-(2,4-dioxo-5-fluoropyrimidine) (Compound 10). The resin was washed with 50% ethanol in water. The product was cleaved from the resin by 1 ml sodium borohydride (1 mmol NaBH$_4$) in 50% ethanol for 4 hours. The eluate was evaporated by rotary evaporator and the product is extracted by isopropanol. L-aspartate alcohol-beta-1N-(2,4-dioxo-5-fluoropyrimidine) was dissolved in water and dried in a lyophilizer.

d. L-aspartate isopropyl amide-beta-1N-(2,4-dioxo-5-fluoropyrimidine) (Compound 11). The product was cleaved from the resin by 5 ml of 5% of isopropyl amine in methanol for 16 hours. The final product was precipitated, and washed several times with diethyl ether and dried. L-aspartate isopropyl amide-beta-1N-(2,4-dioxo-5-fluoropyrimidine) was recrystallized from ethanol.

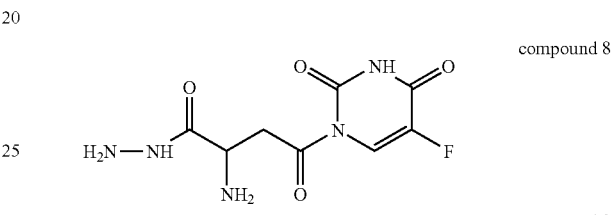

compound 8

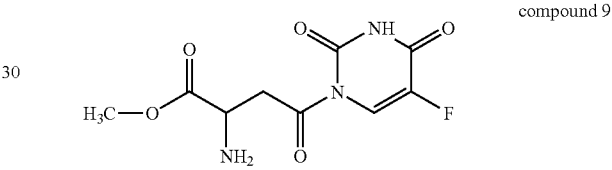

compound 9

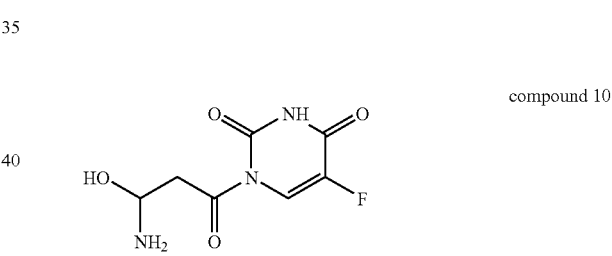

compound 10

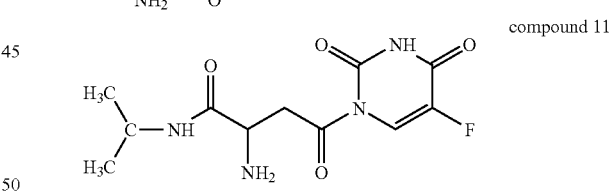

compound 11

Example 9

Synthesis of N-α-Lauroyl-L-aspartic acid-beta-1N-(2,4-dioxo-5-fluoropyrimidine) (Compound 12)

One mmol of Fmoc-Asp-OBut was incubated in 20% piperidine in DMF for 20 minutes. 10-fold volume of diethyl ether was added to the solution. The mixture was cooled and the precipitate of H-Asp-OBut was centrifuged. The precipitate was washed with diethyl ether 3 times. 1.1 mmol of lauroyl chloride was slowly added to the mixture of 1 mmol of H-Asp-OBut and 10 ml phosphate buffer pH 9 for 30 minutes at room temperature, and allowed to shake for another 3 hours. 1N HCl was added drop-wise to pH 6. The precipitate of Lauroyl-Asp-OBut was filtered and washed with water and toluene. 1 mmol of Lauroyl-Asp-OBut was dissolved in 20 ml DCM. The mixture was cooled to 0° C. 1.1 mmol of DCC was dissolved in 10 ml DCM and added to the Lauroyl-Asp-OBut mixture. The reaction was carried out for 30 minutes on cold ice and continued for another 2 hours at room temperature. The white crystals appeared in the mixture were filtered out. 1 mmol of solid 2,4-dioxo-5-fluoropyrimidine was added to the clear solution of activated Lauroyl-Asp-OBut. The reaction was carried out for 20 hours in room temperature. The mixture was filtered and the DCM was evaporated. The product (Lauroyl-Asp(5FU)-OBut) was washed several times with water and ethanol and air-dried. Cleavage of the protecting group (OtBu) was carried out in 1 ml TFA (trifluoroacetic acid)+5% water for 3 hours. The acid was evaporated in a vacuum over KOH pellet. The final product was washed several times with diethyl ether and dried.

N-α-Lauroyl-L-aspartic acid beta-1N-(2,4-dioxo-5-fluoropyrimidine) was recrystallized from methanol+Hexane. Yield of the product was 70% of white crystals. Molecular weight 427 g/mol.

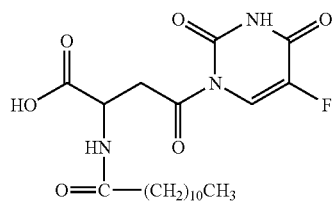

Compound 12: N-α-Lauroyl-L-aspartic acid-beta-1N-(2,4-dioxo-5-fluoropyrimidine)

Example 10

Synthesis of N-α-Palmitoyl-L-glutamic acid-γ-1N-(2,4-dioxo-5-fluoropyrimidine), (Compound 13)

One mmol of Fmoc-Glu-OBut is incubated in 20% piperidine in DMF for 20 minutes. 10-fold of diethyl ether is added to the solution. The mixture is cooled and precipitate of H-Glu-OBut is centrifuged. Precipitate is washed with diethyl ether 3 times. 1.1 mmol of Palmitoyl Chloride is slowly added to the mixture of 1 mmol of H-Glu-OBut and 10 ml phosphate buffer pH 9 for 30 minutes at room temperature, and continued to shake for another 3 hours. 1N HCl is added drop-wise to pH 6. The precipitate of Palmitoyl-Glu-OBut is filtered and washed with water and Toluene. 1 mmol of Palmitoyl-Glu-OBut was dissolved in 20 ml DCM. The mixture is cooled to 0° C. 1.1 mmol of DCC is dissolved in 10 ml DCM and added to the Palmitoyl-Glu-OBut mixture. The reaction was carried out for 30 minutes on cold ice and continued for another 2 hours at room temperature. The white crystals that appeared in the mixture were filtered out. One mmol of solid 2,4-dioxo-5-fluoropyrimidine was added to the clear solution of activated Palmitoyl-Glu-OBut. The reaction is carried out for 20 hours in room temperature. The mixture was filtered and the DCM was evaporated. The product (Palmitoyl-Glu (5FU)-OBut) was washed several times with water and ethanol and air-dried. Cleavage of the protecting group (OtBu) was carried out in 1 ml TFA/5% water for 3 hours. The acid was evaporated in a vacuum over KOH pellet. The final product was washed several times with diethyl ether and dried.

N-α-Palmitoyl-L-glutamic acid γ-1N-(2,4-dioxo-5-fluoropyrimidine) was recrystallized from methanol and hexane. Yield of the product was 52% of white crystals. Molecular weight 497 g/mol.

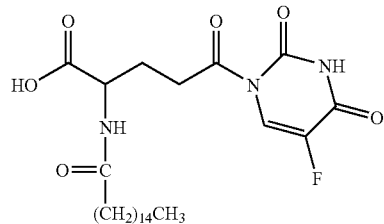

Compound 13: N-α-Palmitoyl-L-glutamic acid-γ-1N-(2,4-dioxo-5-fluoropyrimidine)

Example 11

Synthesis of Aspartyl-beta-1N-(2,4-dioxo-5-fluoropyrimidine)-aspartic acid (Compound 14)

A. Synthesis of Fmoc-Asp(5-FU)-OH

One mmol of Fmoc-Asp-OtBu is dissolved in 20 ml DCM. The mixture is cooled to 0° C. 1.1 mmol of DCC is dissolved in 10 ml DCM and added to the Fmoc-Asp-OtBu mixture. The reaction is carried out for 30 minutes on cold ice and continued for another 2 hours at room temperature. The white crystals that appear in the mixture are filtered out.

One mmol of solid 2,4-dioxo-5-fluoropyrimidine is added to the clear solution of activated Fmoc-Asp-OtBu. The reaction is carried out for 20 hours in room temperature. The mixture is filtered and the DCM is evaporated. The product is washed several times with water and ethanol and air-dried. Cleavage of the protecting groups (OtBu) is carried out in 1 ml TFA+5% water for 3 hours. TFA is evaporated in a vacuum over KOH pellet. Fmoc-Asp(5-FU)-OH is washed several times with diethyl ether and dried.

B. Synthesis of Aspartyl-beta-1N-(2,4-dioxo-5-fluoropyrimidine)-aspartic acid 0.1 g of Fmoc-Asp(OtBu)/Wang resin and 5 ml DMF was shaken for 30 minutes. DMF is filtered and the Fmoc protecting group was removed by incubation in 20% piperidine in DMF 3 times for 10 minutes each time. The resin was washed several times with DMF, DCM. Fmoc-Asp(5-FU)-OH, 10 ml of DMF, 1 mmol of DIC, HOBt were added to AA resin and shaken for 2 hours. The resin was washed with DMF 3 times. Fmoc protecting group was removed by incubation in 20% piperidine in DMF 3 times for 10 minutes each time. The dipeptidyl resin was washed several times with DMF, DCM. Cleavage of the dipeptide and the protecting group (OtBu) was carried out in 1 ml TFA+5% water for 3 hours. The acid was evaporated in a vacuum over KOH pellet. Asp(5-FU)-Asp was washed several times with diethyl ether and dried. Yield of the product was 66% of white crystals. Molecular weight 360 g/mol.

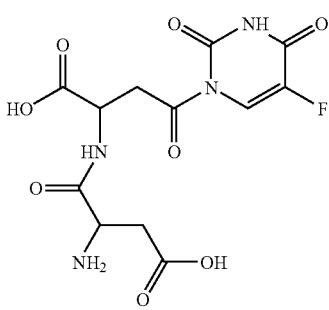

Compound 14: Aspartyl-beta-1N-(2,4-dioxo-5-fluoropyrimidine)-aspartic acid

Example 12

Synthesis of Glutamyl-γ-1N-(2,4-dioxo-5-fluoropyrimidine)-aspartic acid (Compound 15)

Fmoc-Glu(5-FU)-OH is synthesized as described in example 11a for Fmoc-Glu(5-FU)-OH. Binding of Fmoc-Glu (5-FU)-OH to Fmoc-Asp(OtBu)/Wang is synthesized as described in example 11b. Cleavage of dipeptide from resin and of the protecting group (OtBu) was carried out in 1 ml TFA+5% water for 3 hours. The acid was evaporated in a vacuum over KOH pellet. Glu(5-FU)-Asp was washed several times with diethyl ether and dried. Yield of the product was 76% of white crystals. Molecular weight 374 g/mol.

Example 13

Synthesis of Glutamyl-γ-1N-(2,4-dioxo-5-fluoropyrimidine)-glutamic acid (Compound 16)

Fmoc-Glu(5-FU)-OH is synthesized as described in example 11a for Fmoc-Glu(5-FU)-OH. Binding of Fmoc-Glu (5-FU)-OH to Fmoc-Glu(OtBu)/Wang is synthesized as described in example 11b. Cleavage of dipeptide from resin and of the protecting group (OtBu) was carried out in 1 ml TFA+5% water for 3 hours. The acid was evaporated in a vacuum over KOH pellet. Glu(5-FU)-Glu was washed several times with diethyl ether and dried. Yield of the product was 73% of white crystals. Molecular weight 388 g/mol.

Example 14

Synthesis of [Aspartyl-beta-1N-(2,4-dioxo-5-fluoropyrimidine)]$_2$ (Compound 17)

One mmol of Fmoc-Asp-ODmab was dissolved in 20 ml DCM. The solution was cooled to 0° C. 1.1 mmol of DCC was dissolved in 10 ml DCM and added to the Fmoc-Asp-ODmab solution. The reaction was carried out for 30 minutes on cold ice and continued for another 2 hours at room temperature. The white crystals appeared in the solution were filtered out.

One mmol of solid 2,4-dioxo-5-fluoropyrimidine was added to the clear solution of activated Fmoc-Asp-ODmab. The reaction was carried out for 20 hours in room temperature. The mixture was filtered and the DCM was evaporated. The product was washed several times with water and ethanol and air-dried. ODmab protecting group was removed with 2% hydrazine in DMF mixing for 3 minutes. The product Fmoc-Asp(5-FU)-OH was precipitated with 10-fold diethyl ether and washed with ether 3 times. The product Fmoc-Asp(5-FU)-OH was coupled with Cl-Trt-chloride resin. 2-Chlorotrityl-chloride resin (100-200 mesh, 1% DVB), substitution of 1.2 g/mol was swollen in DCM for 1 hour. The resin was washed several times with DCM. 2.4 mmol of Fmoc-Asp(5-FU)-OH was dissolved in 20 ml DCM and added to the resin, 4.8 mmol of diethyl isopropylamine, was added to the reaction. The reaction was carried out for 2 hours at room temperature. The resin was washed several times with DCM, methanol, DCM. Fmoc protecting group was removed by incubation in 20% piperidine in DMF 3 times for 10 minutes each time. The resin was washed several times with DMF, DCM. Fmoc-Asp(5-FU)-OH was added to the mixture of H-Asp(5-FU)-OH/2-Chlorotrityl chloride resin, DIC, HOBt and 10 ml DMF. The mixture was shaken for 3 hours. The resin was washed several times with DMF. Fmoc protecting group was removed by incubation in 20% piperidine in DMF 3 times for 10 minutes each time. The resin was washed several times with DMF, DCM.

Synthesis of [Aspartyl-beta-1N-(2,4-dioxo-5-fluoropyrimidine)]$_2$ is carried out by subsequent steps of coupling and deprotection of Fmoc-Asp(5-FU)-OH on the resin.

Cleavage of the final product from the resin is carried out in 1 ml TFA+5% water for 3 hours. The acid is evaporated in a vacuum over KOH pellet.

The product [Asp(5-FU)]$_2$ was washed several times with diethyl ether and dried. Yield of the product was 54% of white crystals. Molecular weight 472 g/mol.

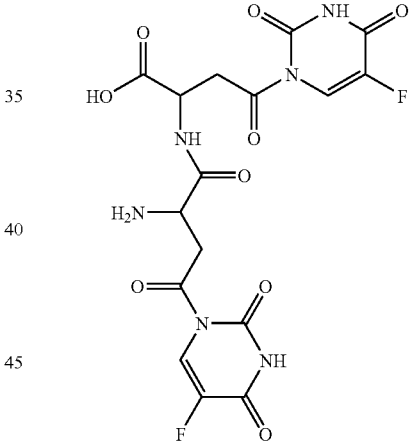

Compound 17: [Aspartyl-beta-1N-(2,4-dioxo-5-fluoropyrimidine)]$_2$

Example 15

Synthesis of [Glutamyl-gamma-1N-(2,4-dioxo-5-fluoropyrimidine)]$_n$ (Compound 18)

Fmoc-Glu(5-FU)-OH was synthesized from Fmoc-Glu-ODmab and 2,4-dioxo-5-fluoropyrimidine as described for Fmoc-Asp(5-FU)-OH in example 14.

Synthesis of (Glutamyl-beta-1N-(2,4-dioxo-5-fluoropyrimidine)$_n$ is carried out by subsequent steps of coupling, deprotection, and cleavage of Fmoc-Glu(5-FU)-OH on the resin as described for Fmoc-Asp(5-FU)-OH in example 14.

The product [Glu(S-FU)]$_2$ yield was 58% with Molecular weight 500 g/mol.

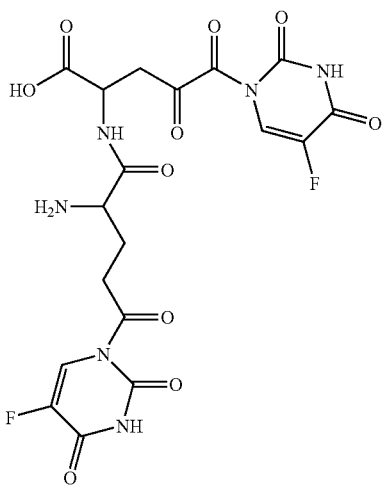

Compound 18: [Glutamyl-beta-1N-(2,4-dioxo-5-fluoropyrimidine)]$_2$

Example 16

Synthesis of Glutamyl-γ-1N-(2,4-dioxo-5-fluoropyrimidine)-glycine (Compound 19)

Fmoc-Glu(5-FU)-OH is synthesized as described in example 11a for Fmoc-Glu(5-FU)-OH. Binding of Fmoc-Glu(5-FU)-OH to Fmoc-Gly/Wang is synthesized as described in example 11b. Cleavage of dipeptide from resin is carried out in 1 ml TFA+5% water for 3 hours. The acid was evaporated in a vacuum over KOH pellet. Glu(5-FU)-Gly was washed several times with diethyl ether and dried. Yield of the product was 72% of molecular weight 316 g/mol.

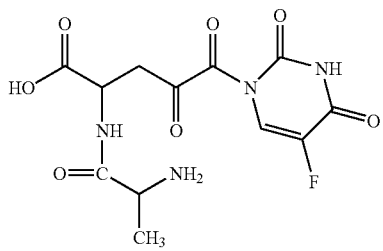

Compound 19: Glutamyl-γ-1N-(2,4-dioxo-5-fluoropyrimidine)-glycine

Example 17

Synthesis of L-aspartic acid and L-glutamic acid Conjugates

Cladribine-beta-L-aspartic acid, Cladribine-beta-L-glutamic acid, Azacytidine-beta-L-aspartic acid, Azacytidine-beta-L-glutamic acid, Cytarabine-beta-L-aspartic acid, Cytarabine-beta-L-glutamic acid, Gemcytabine-beta-L-aspartic acid and Gemcytabine-beta-L-glutamic acid are synthesized as described in example 6.

Example 18

Synthesis of D-Lysine(Melphalan)

One half (0.5) mmol melphalan and 1.5 mmol of triethylamine were dissolved in 5 ml HPLC water. The solution was mixed and 0.6 mmol of S-Boc-2-mercapto-4,6-dimethyl-pirimidine dissolved in 5 ml of dioxane was added. The reaction mixture was mixed for 18 hours. The product, t-Butoxycarbonyl-Melphalan (BOC-Melphalan) was extracted by hexane and precipitated by 0.1N HCl. The precipitate was washed with HPLC water and dissolved in ethanol. Purified Boc-Melphalan was crystallized from ethanol.

One half (0.5) mmol of BOC-Melphalan was dissolved in 10 ml DCM. 0.6 mmol of DCC was dissolved in 5 ml DCM and added to the BOC-Melphalan mixture. The reaction was carried out for 1 hour at room temperature. The white crystals that appeared in the mixture were filtered out. One half (0.5) mmol of solid BOC-Lys-OtBu was added to the clear solution of activated BOC-Melphalan. The reaction was carried out for 20 hours at room temperature. The mixture was filtered and the DCM was evaporated. The product was washed several times with ethanol and air-dried. Cleavage of the protecting groups (BOC, OtBu) was carried out in 1 ml TFA+5% water for 3 hours. The acid was evaporated in a vacuum over a KOH pellet. The final product D-Lys(Melphalan) was washed several times with diethyl ether and dried.

Example 19

Synthesis of D-Lysine(DTPA) metal chelator

DTPA, (diethylene-triaminopentaacetic acid) 0.5 mmol and 1.5 mmol of triethylamine were dissolved in 5 ml HPLC water. The solution was mixed and 1.6 mmol of S-Boc-2-mercapto-4,6-dimethyl-pirimidine dissolved in 5 ml of dioxane was added. The reaction mixture was mixed for 18 hours. The product BOC$_3$(DTPA) was extracted with ethylacetate and saturated citric acid solution. The product was crystallized from ethanol.

One half (0.5) mmol of BOC$_3$(DTPA) was dissolved in 10 ml DCM. 0.6 mmol of DCC was dissolved in 5 ml DCM and added to the BOC$_3$(DTPA) mixture. The reaction was carried out for 1 hour at room temperature. The white crystals that appeared in the mixture were filtered out. 0.5 mmol of solid BOC-Lys-OtBu was added to the reaction. The reaction was carried out for 20 hours at room temperature. The mixture was filtered and the DCM was evaporated. The product was washed several times with ethanol and air-dried. Cleavage of the protecting groups (BOC, OtBu) was carried out in 1 ml TFA (trifluoroacetic acid)+5% water for 3 hours. The acid was evaporated in a vacuum over a KOH pellet. The final product D-Lys(DTPA) was washed several times with diethyl ether and dried. D-Lys(DTPA) was dissolved in water and lyophilized.

Example 20

Synthesis of L-Ornithine(DOTA) metal chelator

DOTA (1,4,7,10-tetraazacyclododecan-1,4,7,10-tetraacetic acid) 0.5 mmol and 1.5 mmol of triethylamine were dissolved in 10 ml DCM. 0.6 mmol of DCC was dissolved in 5 ml DCM and added to the mixture. The reaction was carried out for 1 hour at room temperature. The white crystals that appeared in the mixture were filtered out. 0.5 mmol of solid BOC-Orn-OtBu was added to the reaction. The reaction was carried out for 20 hours at room temperature. The mixture was filtered and the DCM was evaporated. The product was washed several times with ethanol and air-dried. Cleavage of the protecting groups (BOC, OtBu) was carried out in 1 ml TFA+5% water for 3 hours. The acid was evaporated in a vacuum over a KOH pellet. The final product, L-Orn(DOTA), was washed several times with diethyl ether and dried. The product was dissolved in water and lyophilized.

Example 21

In-Vitro Toxicity Profile of Asp(5-FU)

Materials and Methods: Human umbilical vein endothelial cells (HUVEC, normal) cells were grown in M199 medium supplemented with 20% fetal calf serum (FCS), vitamins, 1 ng/ml hbFGF, and antibiotics at 370° C., 5% $CO_2$. Human melanoma cells (WW-94, cancer) cells were grown in 50% DMEM/50% F-12 medium supplemented with 10% fetal calf serum and antibiotics.

The cells were seeded in a 96-well ELISA dish at a concentration of 10,000-20,000 cells/well. The conjugates were added at concentrations that cause IC50 (50% lethality, FIG. 1), or IC90 (90% lethality, FIG. 2) by 5-FU. The cells were incubated for 72 hours at 37° C. and 5% $CO_2$. After 72 hours the medium was aspirated, and DMEM containing 5% FCS and 0.5 mg/ml MTT (3-(4,5-Dimethyl-2-thiazolyl)-2,5-diphenyl-2H-tetrazolium bromide, an indicator of cell viability) was added. The cells were incubated for 2-4 hours at 37° C. and 5% $CO_2$, washed with phosphate buffer saline (PBS) and dissolved in dimethylsulfoxide (DMSO). The results were analyzed using Techan ELISA reader equipped with a 570 nm filter. The results are represented as % of cell mortality.

Figure 2:
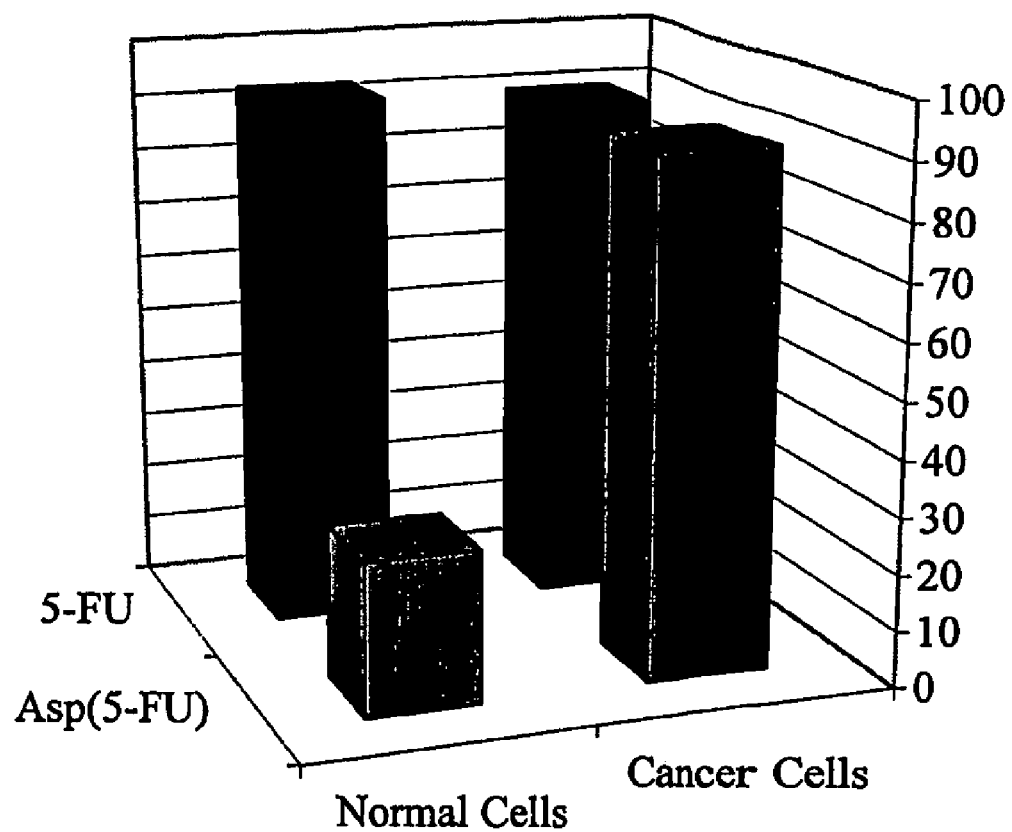
FIG. 2 provides the IC90 toxicity profile of Asp(5-FU) versus 5-FU in normal and malignant cells in culture.

Results: A concentration of 5-FU (black) that causes 50% mortality (IC50) of normal and cancer cells as a free drug did not kill normal cells when administered as a Asp(5-FU) conjugate (gray) as shown in FIG. 1. Furthermore, a concentration of 5-FU that resulted in 90% mortality ($IC_{90}$), caused mortality of only 20% healthy cells when linked to Asp (gray, Asp(5-FU) as shown in FIG. 2. Asp(5-FU) shows a safe treatment profile by reducing toxicity by about 50% to about 70% in comparison to 5-FU.

Example 22

In-Vivo Toxicity in Animal Models: Intravenous Administration

Purpose: To measure the potential acute intravenous (IV) toxicity of Asp(5-FU) in mice, estimated by Maximum Tolerated Dose (MTD) and 50% Lethal Dose ($LD_{50}$).

Method: The potential acute intravenous (IV) toxicity of the Asp(5-FU) was assessed in groups of BALB/c female mice of 5 mice per group, in order to establish appropriate MTD levels towards a projected series of various anti-tumorigenic efficacy trials.

Asp(5-FU) was administered as single IV injections at three dose levels of 80, 150 and 200 mg/kg. One group was administered with saline served as control. In all instances, freshly prepared solutions were injected at a constant volume of 10 ml/kg.

The data relating to 5-FU toxicity in mice was recovered from the National Institute of health (NH) report (Sax, 1987)

Figure 3:
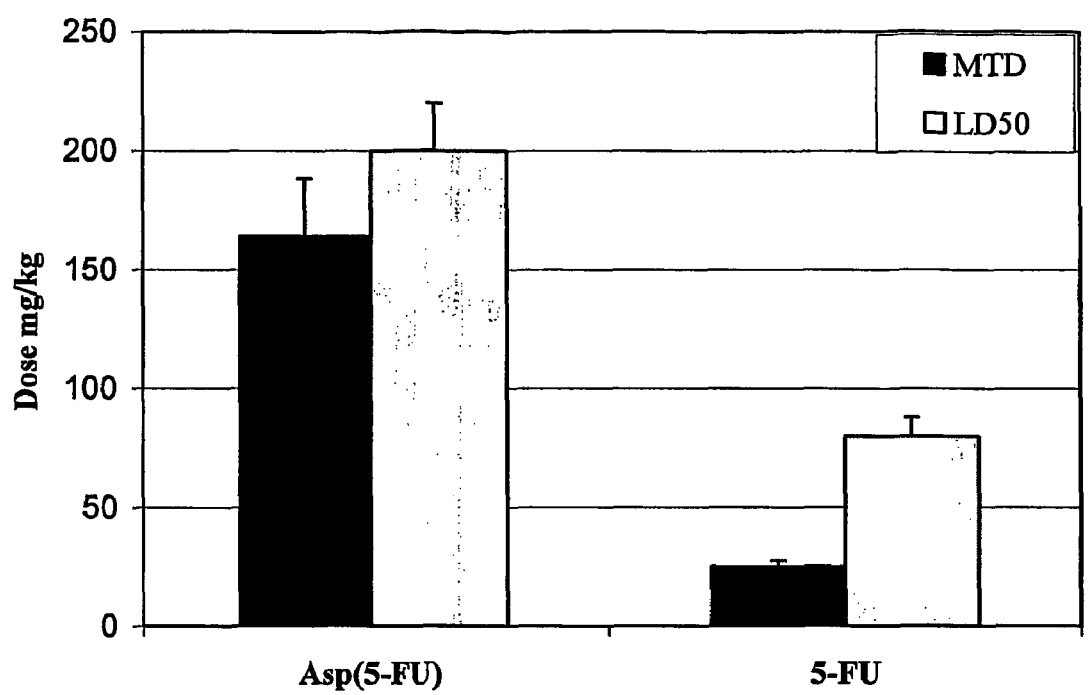
FIG. 3 shows a graph of the maximum tolerated dose (MTD) and $LD_{50}$ toxicity of Asp(5-FU), given intravenously.

Results: Asp(5-FU) was administered as single IV injections at three dose levels of 80, 150 and 200 mg/kg to BALB/c female mice. FIG. 3 shows the increased tolerance (MTD and LD50) of animals to the Asp(5-FU) conjugate compared to the free 5-FU.

Incidence of mortality was confined to the high-dose group of Asp(5-FU) (200 mg/kg), with an incidence of 3/5 mice. Death occurred in the immediate post-dosing period.

No clinical signs in treated animals, other than brief decreased motor activity or lateral recumbency were noted in survivors or decedents respectively, of the high-dose (200 mg/kg). No obvious clinical signs were detected in any of the intermediate- and low-dose (150 & 80 mg/kg, respectively) treated animals and vehicle controls (saline).

Mean group body weights: in the Asp(5-FU) treatment groups a statistically significant (p<0.01) and transient reduced body weight was confined to the intermediate-dose group on Day 8 and was likewise evident by an equally significant reduced body weight gain during the corresponding period. However, a statistically significant (p<0.01) compensatory increase in body weight gain made by these animals during the subsequent study period (Day 8-15) clearly indicated their capacity for full recovery from the earlier noted relative loss of weight. No gross pathological findings were evident in any of the animals at the time of their scheduled necropsy.

In view of the present findings, it may be concluded that 160 mg/kg of Asp(5-FU) represents an appropriate acute intravenous MTD (Maximum Tolerated Dose) level and 200 mg/kg represents LD50 of Asp(5-FU). The data for 5-FU MTD and $LD_{50}$ are 24-26 mg/kg and 81 mg/kg, respectively (NIH report: Dangerous properties of industrial materials reports 1987, p. V8 N6 64).

In conclusion, Asp(5-FU) was shown to be 600% less toxic than 5-FU.

Example 23

In-Vivo Efficacy in Animal Models

Purpose: To evaluate the anticancer activity of Asp(5-FU) of the present invention compared to 5-FU.

The potential anti-tumor activity of Asp(5-FU) was assessed based on the relative growth inhibition of human mammary duct carcinoma, MX-1 murine model.

Propagation of Tumor Material (MX-1 fragments): The Mammary Xenograft-1 (MX-1) is a human derived mammary duct carcinoma, supplied by the National Cancer Institute (NCI). The tissue was kept frozen until the time of implantation. The fragments (one to each animal in the study) were prepared according to the NCI recommended transplantation protocol.

Each vial containing 5 to 6 fragments was rapidly thawed (60-90 seconds) in a water bath at 37-40° C. The frozen fragments were implanted immediately after thawing.

Two fragments were implanted close to each other at the same sub-axillary incision site of each animal assigned to the propagation phase. The mass doubling time of the MX-1 tumor during the logarithmic phase was 4-5 days post implantation. Subsequently, another 2 fragments were implanted into each of 6 animals to achieve at least a total of 20 implanted fragments.

At the end of the logarithmic phase, the donor animals were sacrificed, the tumors were excised, dissected and transferred to a sterile Petri dish placed over ice and cut into approximately 20 fragments (about 2×2×2 mm each) for their transplantation into 10 naïve mice. A total of 42 tumor fragments were transplanted at the end of the second propagation phase. No more than 30 minutes elapsed from the time the tumor was removed from the donor animals until transplantation.

Tumor Induction and Monitoring (Pre-Treatment): Upon completion of the propagation phase, tumor fragments measuring about 2×2×2 mm each, were implanted subcutaneously (SC) into the right flank of each test animal assigned to the main study. Tumor growth was monitored twice weekly and the total SC mass (mm$^3$) determined on the basis of width and length measurement using micrometer calipers. Treatment commenced 10 days following tumor transplantations (Day 10) and after tumors developed a mean group volume of 145-163 mm$^3$ (corresponding to individual tumor volume of 77-258 mm$^3$).

Tumor Growth Monitoring: Monitoring of progressive changes in tumor growth following treatment was carried out twice weekly.

Tumor volume changes were determined using the following equation:

$$V (mm^3) = d^2 (mm^2) \times D (mm)/2$$

wherein $d$ and $D$ represent the smallest and the largest perpendicular tumor diameters respectively.

Clinical Signs: Animals were observed once daily during regular work days for signs of unusual behavior and reactions and with a special emphasis on the tumor development area. Animals were observed for a maximum 5 weeks (treatment period days 1-25 and observation period days 26-35). Observations included changes in skin, fur, eyes, mucous membranes, occurrence of secretions and excretions (e.g. diarrhea) and autonomic activity (e.g. lacrimation, salivation, piloerection, pupil size, unusual respiratory pattern), changes in gait, posture and response to handling, as well as the presence of bizarre behavior, tremors, convulsions, sleep and coma. Animals showing enduring signs of severe distress or animals exhibiting tumor volume of above 2,200 mm$^3$ were humanely killed.

Body Weight: Individual body weights were determined prior to MX-1 fragment transplantation and thereafter once weekly until initiation of treatment. Following initiation of treatment individual body weights were determined twice weekly until the scheduled study termination or in case of removal of animals from the study due to animal welfare reasons, at the time of death.

Blood Sampling: Hematology and biochemistry parameters listed below were determined in all animals assigned to Groups 4, 5 & 6, one day following the last dosing session. Blood samples (at least 100 µl of whole blood, collected into EDTA coated tubes for hematology and at least 200 µl serum, collected into non-coated tubes for biochemistry) were obtained by retro-orbital sinus bleeding under light $CO_2$ anesthesia Following completion of blood collection, all blood and serum samples were kept at 2-8° C. until transferred to the laboratory for analysis.

The examined parameters are as follows: Hematology: WBC, RBC, HGB, HCT, MCV, MCH, MCHC, platelets, differential count. Biochemistry: Creatinine, Calcium, Glucose, Cholesterol, Total protein, Globulin, LDH, Aspartate aminotransferase (AST), Potassium, CPK, Phosphorus, Urea, Amylase, Albumin, Total bilirubin, Alanine aminotransferase (ALT), Sodium, γ-Glutamyl transpeptidase (GGT), Chloride, Triglycerides and Alkaline phosphatase (ALP).

Necropsy Procedures and Macroscopic Examination: Necropsy was performed on all animals including those removed from the study for animal welfare reasons and all surviving 10 days after the last dosing session (Groups 1, 2 & 3), following euthanasia. At necropsy all animals were thoroughly examined for abnormality of tissues or organs and any gross pathological changes. All gross pathological changes were recorded.

Organ/Tissue Fixations: From all animals assigned to Groups 1, 2 & 3 the brain, duodenum, heart, ileum, jejunum, kidneys, liver, lung, pancreas, skeletal muscle (thigh), spleen, sternum (bone marrow) and stomach were fixed and preserved in 10% neutral buffered formalin (approx. 4% formaldehyde solution) for histopathological examination. The individual tumor weight of all tested animals (Groups 1, 2 & 3) was determined and the tumor was preserved as well in 4% formaldehyde.

In addition, any other organs/tissues with gross macroscopic changes were preserved in 4% formaldehyde solution.

Data Evaluation: Final evaluation of the potential antitumor activity was based primarily on relative and comparable inhibition of tumor growth, expressed as mean group values of tumor volume of the Asp(5-FU) treated group vs. the Reference Item treatment group, as well as vs. the vehicle control group. Statistical analysis (Software: GraphPad Instat® version 3.02 Stat. Method: 1-Way ANOVA—Two-Tail P Value Test) was applied to determine significant differences in body weight, hematology and biochemistry parameters, tumor volume and tumor weight.

Animal Care and Use Statement: This study was performed following the review by the Committee for Ethical Conduct in the Care and Use of Laboratory Animals of the Hebrew University, Jerusalem, the IACUC responsible for approving HBI animal usage application and in compliance with its respective registration.

Treatment: (Study Days 10-21)

Route of Administration: The control, test and reference agents were administered by intravenous (IV) injection into one of the tail veins.

Dose and Volume Dosage: the test agent Asp(5-FU) was injected at two dose levels of 50 and 100 mg/kg. Equally sized groups were administered saline or 5-FU (26 mg/kg). In all instances, volume dosage was 10 ml/kg.

Frequency and Duration: Treatment was initiated 10 days following implantation of tumors. Treatment with control, test or reference agents was carried out as 1× daily injection at 3-days inter-dosing intervals ×3.

Results: No mortality occurred in any of the animals prior to the scheduled sacrifice.

Figure 4:
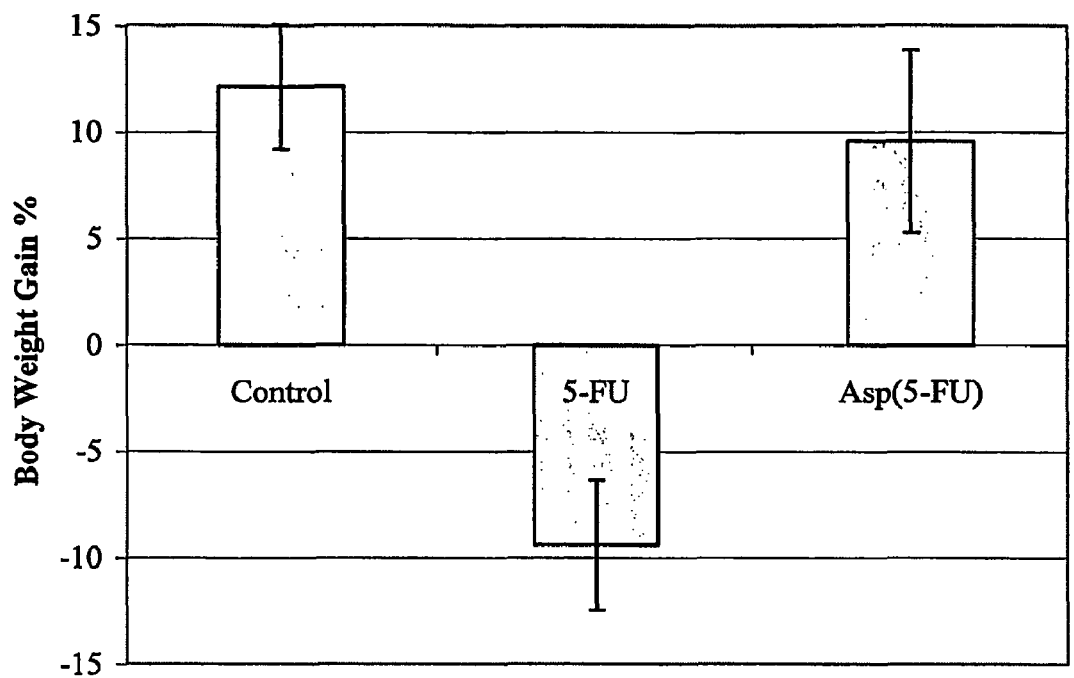
FIG. 4 shows a graph of the body weight changes in xenograft nude mice intravenously treated with Asp(5-FU) or 5-FU.

Comparison of body weight changes of mice treated with Asp(5-FU), 5-FU drug and untreated groups shown in FIG. 4, results are represented in percentage (%) of total body weight.

A significant reduction in tumor progression was noted in Asp(5-FU) treatment groups compared to controls. At the end of the study period, the Asp(5-FU) groups showed a 104% increase in tumor volume compared to 170% and 185% increase for the saline and 5-FU treatment arms, respectively. The results are shown in FIG. 5, represented in volume (mm$^3$) of the tumor through the treatment period.

Figure 5:
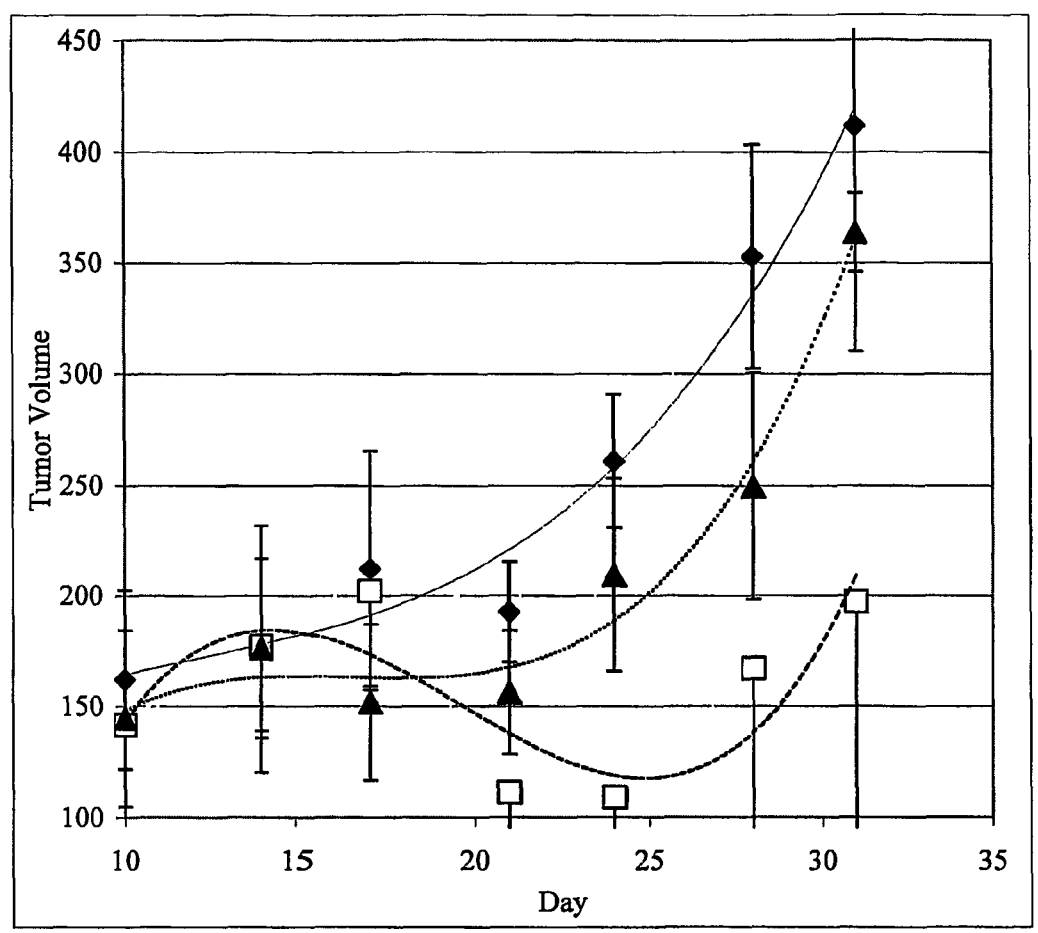
FIG. 5 is a graph showing the progression in tumor volume in xenograft nude mice treated intravenously with Asp(5-FU) or 5-FU.

As shown in FIG. 5, tumor volume progression of MX-1 human mammary duct carcinoma is inhibited significantly by the compound Asp(5-FU) in BALB/c nude mice: Drugs were injected at Days 10, 14 and 18. The drugs represented are Asp(5-FU) (□), 5-FU (▲), and control group (♦). The graph represents tumor progression in volume (mm$^3$) per day. The solid line represents the trend line for the 5-FU treated animals, the dotted line represents the trend line for the control animals and the dashed line represents the trend line for the Asp(5-FU) treated animals.

Figure 6:
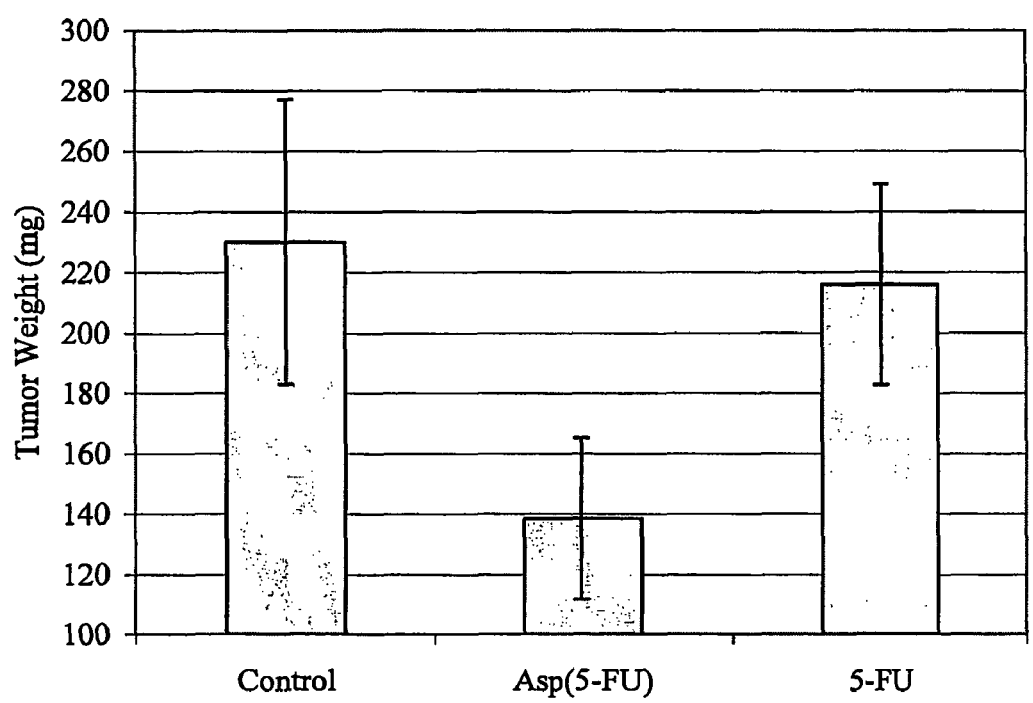
FIG. 6 is a graph depicting the tumor weight (mg) of the malignant xenograft upon necroscopy.

Comparison of tumor weight of Asp(5-FU) treated, 5-FU treated and untreated groups are shown in FIG. 6. The results are represented in weight (mg) of the tumor at the end of the treatment period, following necroscopy.

No gross pathological findings were evident in any of the animals at the time of their scheduled necropsy.

Conclusions: Under the conditions of the present study the findings indicated a significant decrease in progressive tumor volume and weight while treating the animals with Asp(5-FU) compared to treatment with 5-FU and saline control.

Asp(5-FU) shows a more safe and efficient profile than the free 5-FU.

Toxicology tests of Asp(5-FU) in animal models show significant reduction in drug toxicity in respect to maximum tolerated dose (MTD), body weight gain, and pathological signs than free 5-FU.

Asp(5-FU) shows a significantly more efficient profile in reducing tumor volume and weight progression in human cancer xenografts in nude mice than free 5-FU.

Example 24

In-Vivo Toxicity of Oral Administration in Animal Models

OBJECTIVE: To determine the Maximum Tolerated Dose (MTD) of the test product, Asp(5-FU), following a single administration by oral gavage (PO) to mice.

This experiment was performed essentially according to Example 22 supra, with the exception that the test agent and the controls were administered orally, by oral gavage. Asp(5-FU) was suspended in corn oil and administered by single oral gavage (PO), at 2 dose levels of 200 and 400 mg/kg, to 2 test groups. An additional equally sized group was administered the vehicle (corn oil) and served as control. In all instances the volume dosage was 10 ml/kg. Animals were observed for a total duration of 14 days.

No mortality occurred in any of the animals prior to the scheduled necropsy.

No noticeable clinical signs in reaction to dosing were observed in any of the animals immediately post-dosing and throughout the entire 14-day observation period.

Mean group body weight gain of both treatment groups at the end of the 14-day observation period was similar to that of the vehicle control group.

No gross pathological findings were evident in any of the animals at the time of their scheduled necropsy.

In conclusion, the appropriate MTD (Maximum Tolerated Dose) level for the Asp(5-FU) administered in corn oil to mice by a single oral gavage is higher than 400 mg/kg.

Example 25

In-Vivo Efficacy of Oral Administration in Animal Models

This experiment was performed essentially according to Example 23 supra, with the exception that the test agent and the controls were administered orally, by oral gavage.

The compounds were administered to mice following about 3-6 hours food deprivation prior to dosing, using a suitable stainless steel feeding needle. Following dosing, food was withheld for further 1-2 hours.

Dose and Volume Dosage: 50 mg/kg reference item and 200 mg/kg of Asp(5-FU). In all instances, volume dosage was 10 ml/kg.

Frequency and Duration: Treatment with Control, Test or Reference Items was carried out as 1× daily injection at 3-days inter-dosing intervals×7 (days 1-25).

In conclusion, the findings of this experiment indicate a relative decrease in progressive tumor development of the Test Item Asp(5-FU) treated group as compared to the corn oil controls, following seven PO gavage administrations at 3-days inter-dosing intervals, using the human mammary duct carcinoma xenograft MX-1 murine model.

While the present invention has been particularly described, persons skilled in the art will appreciate that many variations and modifications can be made. Therefore, the invention is not to be construed as restricted to the particularly described embodiments, rather the scope, spirit and concept of the invention will be more readily understood by reference to the claims which follow.

REFERENCES

Aslanian A M, Fletcher B S, Kilberg M S, 2001. Asparagine synthetase expression alone is sufficient to induce L-asparaginase resistance in MOLT-4 human leukaemia cells. Biochem J.; 357(Pt 1):321-8.

Barrows, L R, "Antineoplastic and Immunoactive Drugs", Chapter 75, pp 1236-1262, in: Remington: The Science and Practice of Pharmacy, Mack Publishing Co. Easton, Pa., 1995

Brynes, S, Burckart, G J and Mokotoff, M., 1978. Potential inhibitors of L-asparagine biosynthesis. 4. Substituted sulfonamide and sulfonylhydrazide analogs of L-asparagine. J Med Chem. 21(1): 45-9.

Brynes S, Fiorina V J, Cooney D A, Milman H A. 1978. Potential antitumor agents via inhibitors of L-asparagine synthetase: substituted sulfonamides and sulfonyl hydrazides related to glutamine. J Pharm Sci. 67(11): 1550-3.

Capizzi R L, Bertino J R, Handschumacher R E. 1970. L-asparaginase. Ann Rev Med 21:433-444.

Caso G, McNurlan M A, McMillan N D, Eremin O, Garlick P J. 2004. Tumour cell growth in culture: dependence on arginine. Clin Sci (Lond). 107(4):371-9.

Chrzanowski K, Bielawska A, Palka J. 2003. Proline analogue of melphalan as a prodrug susceptible to the action of prolidase in breast cancer MDA-MB 231 cells. Farmaco. 58(11):1113-9.

Fong, W F and Law, C L, 1988. Possible role of the membrane Na+/H+ antiport in ornithine decarboxylase induction by L-asparagine. Biochem Biophys Res Commun, 155(2): 937-942

Hutson R G, Kitoh T, Moraga Amador D A, Cosic S, Schuster S M, Kilberg M S. 1997. Amino acid control of asparagine synthetase: relation to asparaginase resistance in human leukemia cells. Am J Physiol. 272(5 Pt 1):C1691-1699.

McGiven 1998 Biochem J. 330: 255-260.

McLaughlin W H, Thramann W M Jr, Lambrecht R M, Milius R A, Bloomer W D 1988. Preliminary observations of malignant melanoma therapy using radiolabeled alpha-methyltyrosine. J Surg Oncol. 37(3):192-7.

Piek J, Adelt T, Huse K, Bock W J. 1987. Cerebrospinal fluid and plasma aminograms in patients with primary and secondary tumors of the CNS. Infusionsther Klin Ernahr, 14(2): 73-77.

Sax, N. I. 1987. Dangerous Properties of Industrial Material Reports, V8 N6 64.

Sheppard R C, Williams B J, 1982. Acid-labile resin linkage agents for use in solid phase peptide synthesis. Int. J. Peptide Protein Res., 20:451-454.

Stammer, C H and Sato, M, 1978. 5-Carboxamido-4-amino-3-isoxazolidone, an asparagine analog, J Med Chem. 21(7):709-712.

Tandon M, Thomas P D, Shokravi M, Singh S, Samra S, Chang D, Jimbow K. 1998. Synthesis and antitumour effect of the melanogenesis-based antimelanoma agent N-propionyl-4-S-cysteaminylphenol. Biochem Pharmacol. 55(12):2023-9.

Thomas P D, Kishi H, Cao H, Ota M, Yamashita T, Singh S, Jimbow K. 1999. Selective incorporation and specific cytocidal effect as the cellular basis for the antimelanoma action of sulphur containing tyrosine analogs. J Invest Dermatol. 113(6):928-34.

Whitecar J P Jr, Bodey G P, Harris J E, Freireich E J, 1970. L-asparaginase. N Eng J Med, 282: 732-734.

Whitehead R P, Benedetti J K, Abbruzzese J L, Ardalan B, Williamson S, Gaynor E R, Balcerzak S P, Macdonald J S. 2004a. A phase II pilot study of high-dose 24-hour continuous infusion of 5-FU and leucovorin and low-dose PALA for patients with colorectal cancer: a Southwest Oncology Group study. Invest New Drugs; 22(4):467-73.

Whitehead R P, Benedetti J K, Abbruzzese J L, Ardalan B, Goodwin J W, Balcerzak S P, Samlowski W E, Lenz H J, Macdonald J S. 2004b. A phase II study of high-dose 24 hour continuous infusion 5-FU and leucovorin and low-dose PALA for patients with advanced pancreatic adenocarcinoma: a Southwest Oncology Group Study. Invest New Drugs. 22(3):335-41.

What is claimed is:

1. A compound represented by general formula (I):

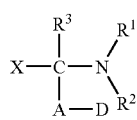
(I)

wherein,
A denotes the side chain of an amino acid, wherein the amino acid is selected from the group consisting of asparagine, glutamine, aspartic acid, or glutamic acid;

D denotes the residue of a pyrimidine or purine antagonist selected from the group consisting of 2,4-dioxo-5-fluoropyrimidine (5-FU), fluorodeoxyuridine (5-FUDR), azacytidine (5-AZC), 6-mercaptopurine (6-MP), 6-thioguanine (6-TG), chlorodeoxyadenosine (2-CDA) and pentostatin (dCF), $R^1$ and $R^2$ are independently selected from a group consisting of hydrogen, a lower alkyl, a $C_1$-$C_{20}$ fatty acid, and a sugar moiety;

$R^3$ is selected from the group consisting of H and lower alkyl; and

X is selected from the group consisting of a carboxyl, an amide, a hydrazide, an ester, a thioester, and an aldehyde.

2. A compound according to claim 1 selected from the group consisting of compounds having general formula (II) and general formula (III):

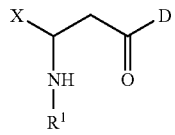
(II)

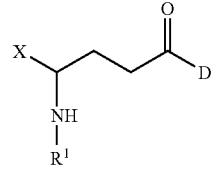
(III)

wherein,
D denotes the residue of a drug selected from the group consisting of a pyrimidine and purine antagonist;

$R^1$ is selected from a group consisting of hydrogen, a lower alkyl, a $C_1$-$C_{20}$ fatty acid, and a sugar moiety; and X is selected from the group consisting of a carboxyl, an amide, a hydrazide, an ester, a thioester, and an aldehyde.

3. The compound according to claim 1, wherein said drug is 2,4-dioxo-5-fluoropyrimidine (5-FU).

4. The compound according to claim 1, wherein X is an ester selected from the group consisting of methyl ester, ethyl ester, propyl ester, iso-propyl ester, butyl ester, iso-butyl ester, tert-butyl ester, tert-pentyl ester, 1-pentyl ester, 2-pentyl ester, 3-pentyl ester, n-hexyl ester, n-heptyl ester, 2-heptyl ester, 1-octyl ester, 2-octyl ester, n-nonyl ester, n-decyl ester, 1-dodecyl ester, 1-myristyl ester, acetyl ester and stearyl ester.

5. The compound according to claim 1, wherein X is a thioester selected from the group consisting of methyl-mercapto ester, ethyl-mercapto ester, n-butyl-mercapto ester, 2-butyl-mercapto ester, tert-butyl-mercapto ester, and n-amyl-mercapto ester.

6. The compound of claim 1, wherein A is the side chain of aspartic acid and D is 2,4-dioxo-5-fluoropyrimidine, the compound having formula IV:

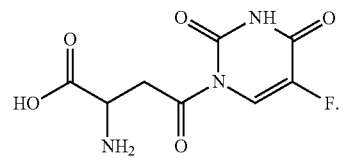
(IV)

7. The compound of claim 1, wherein A is the side chain of aspartamide and D is 2,4-dioxo-5-fluoropyrimidine, the compound having formula V:

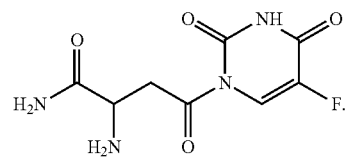
(V)

8. A pharmaceutical composition comprising as an active ingredient, a compound of the general formula (I):

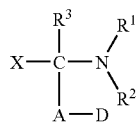

(I)

wherein,

- A denotes the side chain of an amino acid, wherein the amino acid is selected from the group consisting of asparagine, glutamine, aspartic acid, or glutamic acid;
- D denotes the residue of a pyrimidine or purine antagonist selected from the group consisting of 2,4-dioxo-5-fluoropyrimidine (5-FU), fluorodeoxyuridine (5-FUDR), azacytidine (5-AZC), 6-mercaptopurine (6-MP), 6-thioguanine (6-TG), chlorodeoxyadenosine (2-CDA) and pentostatin (dCF),
- $R^1$ and $R^2$ are independently selected from a group consisting of hydrogen, a lower alkyl, a $C_1$-$C_{20}$ fatty acid, and a sugar moiety;
- $R^3$ is selected from H and lower alkyl; and
- X is selected from the group consisting of a carboxyl, an amide, a hydrazide, an ester, a thioester, and an aldehyde; and
- a pharmaceutically acceptable carrier or excipient.

9. The pharmaceutical composition according to claim 8, the group consisting of wherein A is the side chain of aspartic acid and D is 2,4-dioxo-5-fluoropyrimidine, the compound having formula IV:

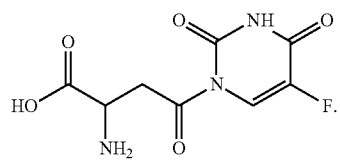

(IV)

10. The pharmaceutical composition according to claim 8, wherein A is the side chain of aspartamide and D is 2,4-dioxo-5-fluoropyrimidine, the compound having formula V:

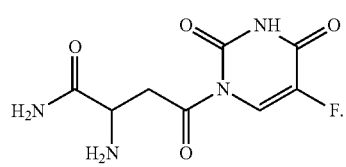

(V)

11. A method of treating a tumor and tumor metastases comprising administering to a subject in need of such treatment a therapeutically effective amount of a compound according to claim 1.

12. A method of treating a tumor and tumor metastases comprising administering to a subject in need of such treatment a therapeutically effective amount of a pharmaceutical composition according to claim 8.

* * * * *